(12) United States Patent  
Oda et al.

(10) Patent No.: US 8,168,638 B2  
(45) Date of Patent: May 1, 2012

(54) PYRAZINECARBOXAMIDE DERIVATIVES AND PLANT DISEASE CONTROLLING AGENTS CONTAINING THE SAME

(75) Inventors: Masatsugu Oda, Kawachinagano (JP); Takashi Furuya, Kawachinagano (JP); Motohiro Hasebe, Kawachinagano (JP); Nobutaka Kuroki, Kawachinagano (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 871 days.

(21) Appl. No.: 12/086,582

(22) PCT Filed: Dec. 21, 2006

(86) PCT No.: PCT/JP2006/326180  
§ 371 (c)(1), (2), (4) Date: Aug. 21, 2008

(87) PCT Pub. No.: WO2007/072999  
PCT Pub. Date: Jun. 28, 2007

(65) Prior Publication Data  
US 2009/0233934 A1  Sep. 17, 2009

(30) Foreign Application Priority Data

Dec. 22, 2005 (JP) .................. 2005-370863  
Feb. 24, 2006 (JP) .................. 2006-049068  
Oct. 10, 2006 (JP) .................. 2006-276601

(51) Int. Cl.  
*A01N 43/60* (2006.01)  
*A01P 3/00* (2006.01)  
*C07D 241/16* (2006.01)  
*C07D 241/24* (2006.01)

(52) U.S. Cl. ............ 514/252.1; 544/336; 424/405

(58) Field of Classification Search .......... 544/336; 514/252.1  
See application file for complete search history.

(56) References Cited

U.S. PATENT DOCUMENTS  
2008/0064708 A1  3/2008 Furuya et al.  
2008/0085924 A1  4/2008 Dunkel et al.

FOREIGN PATENT DOCUMENTS  
WO  2004/054982  7/2004  
WO  2004/058723  7/2004  
WO  2005/115994  12/2005

OTHER PUBLICATIONS

International Search Report issued Mar. 26, 2007 in the International (PCT) Application of which the present application is the U.S. National Stage.

*Primary Examiner* — David J Blanchard  
*Assistant Examiner* — Kortney L Klinkel  
(74) *Attorney, Agent, or Firm* — Wenderoth, Lind & Ponack, L.L.P.

(57) ABSTRACT

The present invention provides the compounds represented by the general formula (I):

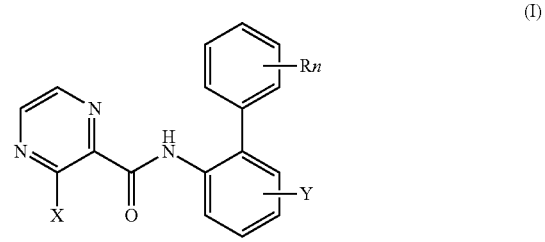

(I)

[wherein X is a halogen atom or an ($C_1$-$C_3$)alkyl group which may be substituted with a halogen atom(s); Y is a hydrogen or halogen atom, or a cyano, a ($C_1$-$C_3$)alkyl or ($C_1$-$C_3$)alkoxy group; R is a hydrogen or halogen atom, a cyano group, or a ($C_1$-$C_6$)alkyl, ($C_2$-$C_6$)alkenyl group, ($C_2$-$C_6$)alkynyl, ($C_1$-$C_6$)alkoxy, ($C_2$-$C_6$)alkenyloxy, ($C_2$-$C_6$)alkynyloxy, ($C_1$-$C_6$)alkylthio, ($C_1$-$C_6$)alkylsulfinyl or ($C_1$-$C_6$)alkylsulfonyl group which may be substituted with a halogen atom(s), a ($C_1$-$C_6$)alkoxycarbonyl group, a ($C_1$-$C_6$)alkoxyimino($C_1$-$C_3$)alkyl group, a tri($C_1$-$C_{10}$)alkylsilyl group, or a phenyl, phenoxy, pyridyloxy or pyrimidyloxy group which may be substituted with a substituent(s); n is an integer of 1 to 5], which compounds cause reduced loads of deleterious, harmful effects to the earth environment, and exhibit a widened controlling spectrum at lowered chemical application rates, thereby finding useful application as a plant disease controlling agent for agricultural and horticultural uses.

16 Claims, No Drawings

PYRAZINECARBOXAMIDE DERIVATIVES AND PLANT DISEASE CONTROLLING AGENTS CONTAINING THE SAME

This application is a U.S. national stage of International Application No. PCT/JP2006/326180 filed Dec. 21, 2006.

TECHNICAL FIELD

The present invention relates to pyrazinecarboxamide derivatives or their salts, and to plant disease controlling agents for agricultural and horticultural uses which contain the said compound as an active ingredient.

BACKGROUND ART

Certain pyrazinecarboxamide derivatives are heretofore known to exhibit pest-controlling activity (for example, refer to the Official Gazette of JP-A Hei 2-175 and the Pamphlet of PCT 05/115994). Also, some biphenyl compounds are found to be effective for controlling the destructive or injurious fungi (for example, refer to the Official Gazette of Japanese Patent No. 3202079).

DISCLOSURE OF INVENTION

The Problem that the Invention is Intended to Solve

However, various problems have been left unsolved, as may be reflected by the problems being encountered in that the compounds described in the Official Gazette of JP-A Hei 2-175, do not exhibit any practically useful activity against gray mould disease and powdery mildew, and the compounds mentioned in the Pamphlet of WO 05/115994 show acaricidal activity but decreased bactericidal or fungicidal activity, while those described in the Official Gazette of Japanese Patent No. 3202079 not only exhibit reduced activity against powdery mildew but also fail to elicit any practically useful activity against the diseases caused by the fungi of the Basidomycetes class, such as leaf rust of a wheat plant and sheath blight of a rice plant. As has been delineated above, the compounds pertaining to the prior art have not always been found to be satisfactory as a plant disease controlling agent for agricultural and horticultural uses in terms of the efficacy and the width of pest-controlling spectrum. In recent years, intensified attention has been focused on the recently mounting loads of deleterious, harmful effects to the earth environment, and in the field of plant disease controlling agents or formulations for agricultural and horticultural uses, likewise, this has resulted in currently strengthened demands for the compounds which possess a widened pest-controlling spectrum at lowered application rates.

Means for Solving the Problems

The present inventors, with a specific view to solving the above-described problems, conducted repeatedly intensive research studies, and as a result, found that a pyrazinecarboxamide derivative represented by the general formula (I) and its salts according to the present invention, when processed into a plant disease controlling agent for agricultural and horticultural uses, do not only produce improved pest controlling effects but also show the extremely widened fungicidal spectrum, thus culminating into completion of the present invention. Namely, the present invention relates to:

1) A pyrazinecarboxamide derivative, or its salts, represented by the general formula (I):

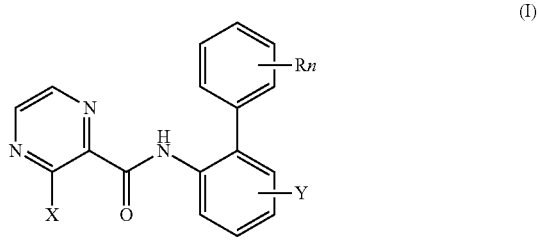

(I)

[wherein X is a halogen atom or an $(C_1-C_3)$alkyl group which may be substituted with a halogen atom(s); Y is a hydrogen or halogen atom, or a $(C_1-C_3)$alkyl or $(C_1-C_3)$alkoxy group; R is a hydrogen or halogen atom, a cyano group, a $(C_1-C_6)$alkyl group which may be substituted with a halogen atom(s), a $(C_2-C_6)$alkenyl group which may be substituted with a halogen atom(s), a $(C_2-C_6)$alkynyl group which may be substituted with a halogen atom(s) or hydroxy group, a $(C_1-C_6)$alkoxy group which may be substituted with a halogen atom(s), a $(C_2-C_6)$alkenyloxy group which may be substituted with a halogen atom(s), a $(C_2-C_6)$alkynyloxy group which may be substituted with a halogen atom(s), a $(C_1-C_6)$alkylthio group which may be substituted with a halogen atom(s), a $(C_1-C_6)$alkylsulfinyl group which may be substituted with a halogen atom(s), a $(C_1-C_6)$alkylsulfonyl group which may be substituted with a halogen atom(s), a $(C_1-C_6)$alkoxycarbonyl group or $(C_1-C_6)$alkoxyimino$(C_1-C_3)$alkyl group, a tri$(C_1-C_{10})$alkylsilyl group in which the $(C_1-C_{10})$ alkyl groups may be the same or different, a phenyl group which may be substituted with a substituent(s) Z (where Z is to be defined below), a phenoxy group which may be substituted with a substituent(s) Z (where Z is to be defined below), a pyridyloxy group which may be substituted with a substituent (s) Z (where Z is to be defined below), or a pyrimidyloxy group which may be substituted with a substituent(s) Z (where Z is to be defined below); n is an integer of 1 to 5; when n is an integer of 2 to 5, R may be the same or different and the two adjacent Rs can be taken together to represent a $(C_3-C_5)$ alkylene group which may be substituted with a substituent(s) Z (where Z is to be defined below), $(C_2-C_4)$alkyleneoxy group which may be substituted with a substituent(s) Z (where Z is to be defined below), $(C_2-C_4)$alkenyleneoxy group which may be substituted with a substituent(s) Z (where Z is to be defined below), or a $(C_1-C_3)$alkylenedioxy group which may be substituted with a substituent(s) Z (where Z is to be defined below); Z is a hydrogen or halogen atom, a cyano group, a $(C_1-C_6)$alkyl group which may be substituted with a halogen atom(s), a $(C_2-C_6)$alkenyl group which may be substituted with a halogen atom(s), a $(C_2-C_6)$alkynyl group which may be substituted with a halogen atom(s), a $(C_1-C_6)$alkoxy group which may be substituted with a halogen atom(s), a $(C_2-C_6)$ alkenyloxy group which may be substituted with a halogen atom(s), a $(C_2-C_6)$alkynyloxy group which may be substituted with a halogen atom(s), a $(C_1-C_6)$alkylthio group which may be substituted with a halogen atom(s), a $(C_1-C_6)$alkylsulfinyl group which may be substituted with a halogen atom(s), a $(C_1-C_6)$alkylsulfonyl group which may be substituted with a halogen atom(s), or a $(C_1-C_6)$alkoxycarbonyl, $(C_1-C_6)$alkoxyimino$(C_1-C_3)$alkyl or carbamoyl group, and when a plural number of Zs are present, the Zs may be the same or different].

2) The pyrazinecarboxamide derivative or its salts as described above under the item 1), wherein X is a chlorine, bromine or iodine atom, or a methyl, fluoromethyl, difluoromethyl or trifluoromethyl group.

3) The pyrazinecarboxamide derivative or its salts as described above under the item 1) or 2), wherein R is a hydrogen or halogen atom, a cyano group, a $(C_1$-$C_6)$alkyl group which may be substituted with a halogen atom(s), a $(C_2$-$C_6)$alkenyl group which may be substituted with a halogen atom(s), a $(C_2$-$C_6)$alkynyl group which may be substituted with a halogen atom(s), a $(C_1$-$C_6)$alkoxy group which may be substituted with a halogen atom(s), a $(C_2$-$C_6)$alkenyloxy group which may be substituted with a halogen atom(s), a $(C_2$-$C_6)$alkynyloxy group which may be substituted with a halogen atom(s), a $(C_1$-$C_6)$alkylthio group which may be substituted with a halogen atom(s), a $(C_1$-$C_6)$alkylsulfinyl group which may be substituted with a halogen atom(s), a $(C_1$-$C_6)$alkylsulfonyl group which may be substituted with a halogen atom(s), or a $(C_1$-$C_6)$alkoxycarbonyl group; when n is an integer of 2 to 5, R may be the same or different, or the two adjacent Rs are taken together to represent a $(C_3$-$C_5)$ alkylene or $(C_2$-$C_4)$alkyleneoxy group, or a $(C_1$-$C_3)$alkylenedioxy group which may be substituted with a halogen atom(s).

4) The pyrazinecarboxamide derivatives or their salts as described above under any one of the items 1) to 3), wherein Y is a hydrogen atom.

5) A plant disease controlling agent for agricultural and horticultural uses, characterized in that said plant disease controlling agent contains as an active ingredient the pyrazinecarboxamide derivative or its salts as described above under any one of the items 1) to 4).

6) A method for controlling a plant disease, characterized in that said method comprises treating a targeted plant or soil with an effective amount of the pyrazinecarboxamide derivative or its salts as described above under any one of the items 1) to 4).

Effect of the Invention

The present invention provides the compounds, which possess improved action performance, as compared with the compounds pertaining to the prior art, and especially as a plant disease controlling agent for agricultural and horticultural uses, develop a widened pest controlling spectrum at lowered application rates.

BEST MODE FOR CARRYING OUT THE INVENTION

Referring to the definitions laid down for the general formula (I) representing the pyrazinecarboxamide derivatives of the present invention, the "halogen atom" includes, for example, a fluorine, chlorine, bromine or iodine atom; the "$(C_1$-$C_6)$alkyl group which may be substituted with a halogen atom(s)" is exemplified by straight-chain or branched alkyl groups of 1 to 6 carbon atoms, such as methyl, ethyl, n-propyl, isopropyl, n-butyl, isobutyl, sec-butyl, tert-butyl, n-pentyl, neopentyl, n-hexyl groups, etc., and straight-chain or branched alkyl groups of 1 to 6 carbon atoms being substituted with not less than one halogen atom which may be the same or different, such as fluoromethyl, difluoromethyl, trifluoromethyl, perfluoroethyl, perfluoroisopropyl, chloromethyl, bromomethyl, 1-bromoethyl, 2,3-dibromopropyl groups, etc.; the "$(C_2$-$C_4)$alkenyl" includes, for example, straight-chain or branched alkenyl groups of 1 to 6 carbon atoms, such as vinyl, allyl, isopropenyl, 1-butenyl, 2-butenyl, 1-methyl-2-propenyl, 2-methyl-1-propenyl, pentenyl, 1-hexenyl groups, etc.; the "$(C_2$-$C_6)$alkynyl group" is exemplified by straight-chain or branched alkynyl groups of 2 to 6 carbon atoms, such as ethynyl, 1-propynyl, 2-propynyl, 1-butynyl, 2-butynyl, 3-butynyl, 3-methyl-1-propynyl, 2-methyl-3-propynyl, pentynyl, 1-hexynyl groups, etc.; and the "$(C_1$-$C_6)$ alkoxy group" includes, for example, straight-chain or branched alkoxy groups of 1 to 6 carbon atoms, such as methoxy, ethoxy, n-propoxy, isopropoxy, n-butoxy, sec-butoxy, t-butoxy, n-pentyloxy, isopentyloxy, neopentyloxy, n-hexyloxy groups, etc.; the "$(C_2$-$C_6)$alkenyloxy group" is exemplified by straight-chain or branched alkenyloxy groups of 2 to 6 carbon atoms, such as propenyloxy, butenyloxy, pentenyloxy groups, etc.; the term "$(C_2$-$C_6)$alkynyloxy group" includes, for example, straight-chain or branched alkynyloxy groups of 2 to 6 carbon atoms, such as propynyloxy, butynyloxy, pentynyloxy groups, etc.; the "$(C_1$-$C_6)$ alkylthio group" includes, for example, straight-chain or branched alkylthio groups of 1 to 6 carbon atoms, such as methylthio, ethylthio, n-propylthio, isopropylthio, n-butylthio, sec-butylthio, t-butylthio, n-pentylthio, isopentylthio, n-hexylthio groups, etc.; the "$(C_1$-$C_6)$alkylsulfinyl group" includes, for example, straight-chain or branched alkylsulfinyl groups of 1 to 6 carbon atoms, such as methylsulfinyl, ethylsulfinyl, n-propylsulfinyl, isopropylsulfinyl, n-butylsulfinyl, sec-butylsulfinyl, t-butylsulfinyl, n-pentylsulfinyl, isopentylsulfinyl, n-hexylsulfinyl groups, etc.; the "$(C_1$-$C_6)$ alkylsulfonyl group" includes, for example, straight-chain or branched alkylsulfonyl groups of 1 to 6 carbon atoms, such as methylsulfonyl, ethylsulfonyl, n-propylsulfonyl, isopropylsulfonyl, n-butylsulfonyl sec-butylsulfonyl, t-butylsulfonyl, n-pentylsulfonyl, isopentylsulfonyl, n-hexylsulfonyl groups, etc.; the "$(C_1$-$C_6)$alkoxycarbonyl group" includes, for example, straight-chain or branched alkoxycarbonyl groups of 1 to 6 carbon atoms, such as methoxycarbonyl, ethoxycarbonyl, n-propoxycarbonyl, isopropoxycarbonyl, n-butoxycarbonyl, t-butoxycarbonyl groups, etc.; the "$(C_1$-$C_6)$alkoxyimino$(C_1$-$C_3)$alkyl group" includes, for example, straight-chain or branched $C_1$-$C_6$ alkoxyimino$(C_1$-$C_3)$alkyl groups, such as methoxyiminomethyl, ethoxyiminomethyl, n-propoxyiminomethyl, isopropoxyiminomethyl groups, etc.; the "tri$(C_1$-$C_{10})$alkylsilyl group" includes, for example, straight-chain or branched alkylsilyl groups of 1 to 10 carbon atoms, such as trimethylsilyl, triethylsilyl groups, etc.; the "tri$(C_1$-$C_{10})$alkylsilyl group" has three $(C_1$-$C_{10})$ groups which may be the same or different; the "$(C_3$-$C_5)$alkylene group" is exemplified by straight-chain or branched alkylene groups of 3 to 5 carbon atoms, such as propylene, butylene, pentamethylene groups, etc.; the "$(C_2$-$C_4)$alkyleneoxy group" includes, for example, straight-chain or branched alkyleneoxy groups of 2 to 4 carbon atoms, such as ethyleneoxy, propyleneoxy, butyleneoxy groups, etc.; the "$(C_1$-$C_3)$alkylenedioxy group" is exemplified by straight-chain or branched alkylenedioxy groups of 1 to 3 carbon atoms, such as methylenedioxy, ethylenedioxy, propylenedioxy groups, etc.

The above-mentioned $(C_2$-$C_6)$alkenyl groups, $(C_2$-$C_6)$ alkynyl groups, $(C_1$-$C_6)$alkoxy groups, $(C_2$-$C_6)$alkenyloxy groups, $(C_2$-$C_6)$alkynyloxy groups, $(C_1$-$C_6)$alkylthio groups, $(C_1$-$C_6)$alkylsulfinyl groups, $(C_1$-$C_6)$alkylsulfonyl groups or $(C_1$-$C_3)$alkylenedioxy groups may be substituted with one or not less than two halogen atoms at any substitutable positions. In the case of substitution with not less than two halogen atoms, such halogen atoms may be the same or different.

The salts of the pyrazinecarboxamide derivatives according to the present invention as represented by the general formula (I) may be exemplified by inorganic acid salts, such as hydrochlorides, sulfates, nitrates, phosphates, etc., organic acid salts, such as acetates, fumarates, maleates, oxalates, methanesulfonates, benzensulfonates, p-toluenesulfonates, etc., and salts formed with inorganic or organic ions, such as sodium ion, potassium ion, calcium ion, trimethylammonium, etc.

In the compounds according to the present invention as represented by the general formula (I), X is preferably chlorine, bromine or iodine atom, or a methyl, fluoromethyl, difluoromethyl or trifluoromethyl group, and more preferably a trifluoromethyl group.

Y is preferably a hydrogen or halogen atom, or a methyl group, and more preferably a hydrogen atom.

R is preferably a hydrogen atom, a halogen atom, such as chlorine, bromine and iodine atoms, etc., a cyano group, a $(C_1-C_6)$alkyl group which may be substituted with a halogen atom(s), a $(C_2-C_6)$alkenyl group which may be substituted with a halogen atom(s), a $(C_2-C_6)$alkynyl group which may be substituted with a halogen atom(s), a $(C_1-C_6)$alkoxy group which may be substituted with a halogen atom(s), a $(C_2-C_6)$alkenyloxy group which may be substituted with a halogen atom(s), a $(C_2-C_4)$alkynyloxy group which may be substituted with a halogen atom(s), a $(C_1-C_6)$alkylthio group which may be substituted with a halogen atom(s), a $(C_1-C_6)$alkylsulfinyl group which may be substituted with a halogen atom(s), a $(C_1-C_6)$alkylsulfonyl group which may be substituted with a halogen atom(s), or a $(C_1-C_6)$alkoxycarbonyl group, or when n is not less than 2, R may be the same or different and the two adjacent Rs are taken together to represent a $(C_3-C_5)$alkylene or $(C_2-C_4)$alkyleneoxy group or a $(C_1-C_3)$alkylenedioxy group which may be substituted with a halogen atom(s). R is more preferably a halogen atom, such as chlorine, bromine and iodine atoms, etc., a cyano group, a $(C_1-C_4)$alkyl group which may be substituted with a halogen atom(s), a $(C_2-C_4)$alkenyl group which may be substituted with a halogen atom(s), a $(C_2-C_4)$alkynyl group which may be substituted with a halogen atom(s), a $(C_1-C_4)$alkoxy group which may be substituted with a halogen atom(s), a $(C_2-C_4)$alkenyloxy group which may be substituted with a halogen atom(s), a $(C_2-C_4)$alkynyloxy group which may be substituted with a halogen atom(s), a $C_1-C_4$alkylthio group which may be substituted with a halogen atom(s), a $(C_1-C_4)$alkylsulfinyl groups which may be substituted with a halogen atom(s), or a $(C_1-C_4)$alkylsulfonyl group which may be substituted with a halogen atom(s), or when n is not less than 2, R may be the same or different and the two adjacent Rs are taken together to represent $(C_1-C_3)$alkylenedioxy groups which may be substituted with a halogen atom(s).

n is preferably an integer of 1 to 3.

The compounds of the present invention can be produced, for example, in accordance with the below-described Production Processes 1 and 2, but no restriction is understood to be posed on these production processes.

Production Process 1:

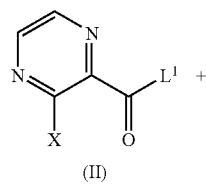

(II)

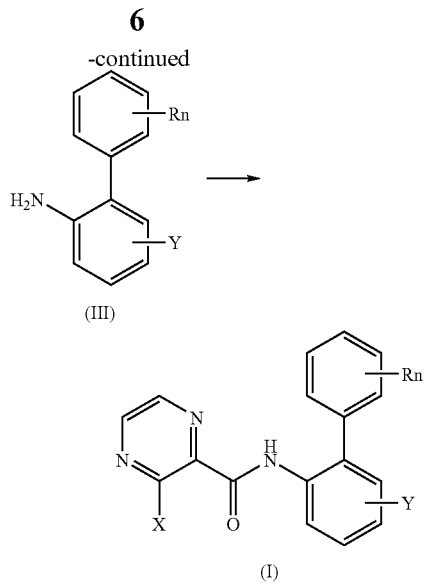

(wherein X, Y, R and n are as defined above, and $L^1$ is a leaving group, such as a chlorine or bromine atom, alkoxy groups, etc.).

A pyrazinecarboxylic acid derivative represented by the general formula (II) can be reacted with a 2-aminobiphenyl derivative represented by the general formula (III) in an inert solvent in the presence of a base to produce a pyrazinecarboxamide derivative of the present invention as represented by the general formula (I). In the present reaction, the reaction temperature is normally in the range of about −20° C. to 120° C., while the reaction time is generally in the range of about 0.2 to 24 hours. An aminobiphenyl derivative represented by the general formula (III) is normally used in proportions of about 0.2 to 5 moles per mole of a pyrazinecarboxylic acid derivative represented by the general formula (II).

As the base, there may be mentioned, for example, inorganic bases, such as sodium hydroxide, potassium hydroxide, sodium carbonate, potassium carbonate, sodium hydrogencarbonate, potassium hydrogencarbonate, etc., acetic acid salts, such as sodium acetate, potassium acetate, etc., alkali metal alkoxides, such as potassium t-butoxide, sodium methoxide, sodium ethoxide, etc., tertiary amines, such as triethylamine, diisopropylethylamine, 1,8-diazabicyclo-[5.4.0]undec-7-en, etc., nitrogen-containing aromatic compounds, such as pyridine, dimethylaminopyridine, etc., and the like. The base is generally used in proportions of about 0.5 to 10 moles per mole of a pyrazinecarboxylic acid derivative represented by the general formula (II). The inert solvent which can be used may be any inert solvents, unless they hinder or inhibit markedly the present reaction, and such solvents can be exemplified by alcohols, such as methanol, ethanol, propanol, butanol, 2-propanol, etc., straight-chain or cyclic ethers, such as diethyl ether, tetrahydrofuran, dioxane, etc., aromatic hydrocarbons, such as benzene, toluene, xylene, etc., halogenated hydrocarbons, such as methylene chloride, chloroform, carbon tetrachloride, etc., halogenated aromatic hydrocarbons, such as chlorobenzene, dichlorobenzene, etc., nitrites, such as acetonitrile, etc., esters, such as ethyl acetate, etc., polar solvents, such as N,N-dimethylformamide, N,N-dimethylacetamide, dimethyl sulfoxide, 1,3-dimethyl-2-imidazolidinone, water, acetic acid, etc., and the like. These inert solvents can be used solely or as a mixture of not less than two thereof.

The pyrazinecarboxylic acid derivatives represented by the general formula (II) which are usable in the present reaction are the known compounds, and the pyrazinecarboxylic acid derivative of the general formula (II') where X is for example a trifluoromethyl group can be produced, for example, by the process as depicted in the below-described Reference Preparation Procedures 1 to 8.

Reference Preparation Procedure 1:

(wherein hal is a halogen atom; $R^1$ is a hydrogen atom or a $(C_1-C_6)$alkyl group; Me is a methyl group).

In accordance with a procedure similar to the ones described in the known literature references (for example, refer to the Pamphlet of WO 05/115994 and J. Heterocycl. Chem., 34, 551 (1997)), a halogenated pyrazinecarboxylic acid derivative represented by the general formula (II-1) can be reacted with methyl chlorodifluoroacetate in the presence of potassium fluoride to produce a trifluoromethyl-pyrazinecarboxylic acid derivative represented by the general formula (II').

Reference Preparation Procedure 2:

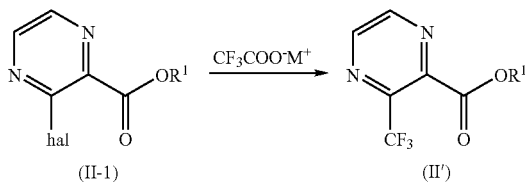

(wherein hal and $R^1$ are as defined above; M is an alkali metal atom or $NHR^1_3$ (wherein $R^1$ is as defined above)).

In accordance with a procedure similar to the ones described in the known literature references (for example, refer to J. Chem. Soc. Perkin Trans I, 1988, 921, Chem. Lett., 12, 1719 (1981) and the Official Gazette of U.S. Pat. No. 4,814,480), a halogenated pyrazinecarboxylic acid derivative represented by the general formula (II-1) can be reacted with a trifluoroacetic acid salt to produce a trifluoromethylpyrazinecarboxylic acid derivative represented by the general formula (II').

Reference Preparation Procedure 3:

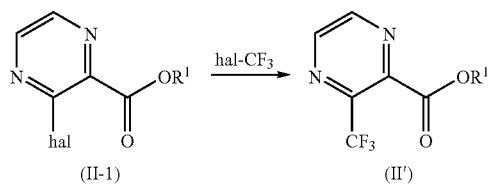

(wherein hal and $R^1$ are as defined above).

In accordance with a procedure similar to the ones described in the known literature reference (for example, refer to J. Med. Chem., 27 (3), 255 (1984), J. Chem. Soc. Chem. Commun., (1992) 1, 53 and J. Chem. Soc. Chem. Commun., 1988, 638), a halogenated pyrazinecarboxylic acid derivative represented by the general formula (II-1) can be reacted with a halogenated trifluoromethyl to produce a trifluoromethylpyrazinecarboxylic acid derivative represented by the general formula (II').

Reference Preparation Procedure 4:

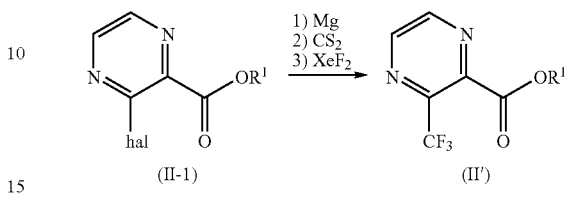

(wherein hal and $R^1$ are as defined above).

In accordance with a procedure similar to the ones described in the known literature references (for example, refer to Tetrahedron Letters, vol. 31 (23), 3357 (1990)), a halogenated pyrazinecarboxylic acid derivative represented by the general formula (II-1) is reacted with magnesium to be converted to a Grignard reagent, and the said Grignard reagent can be reacted with carbon disulfide, followed by reaction with xenon fluoride to produce a trifluoromethyl-pyrazinecarboxylic acid derivative represented by the general formula (II').

Reference Preparation Procedure 5:

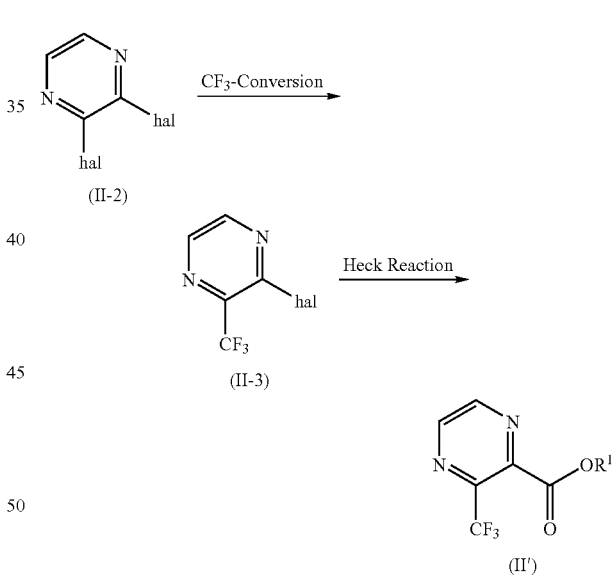

(wherein hal and $R^1$ are as defined above).

In accordance with the procedures as described in Reference Preparation Procedures 1 to 4, 2,3-dihalogenated pyrazines represented by the general formula (II-2) can be subjected to substitution of either one of their halogen atoms with a trifluoromethyl group to give trifluoromethylpyrazines represented by the general formula (II-3), followed by conversion of the remaining halogen atom to a carboxylic acid or its ester through Heck reaction (for example, refer to the Official Gazettes of JP-A Nos. Sho 64-000047, Hei 8-157421 and Hei 9-151156) to produce trifluoromethylpyrazinecarboxylic acid derivatives represented by the general formula (II').

Reference Preparation Procedure 6:

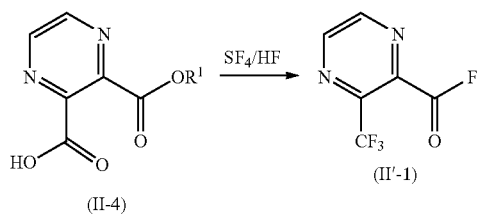

(wherein hal and $R^1$ are as defined above).

In accordance with a procedure similar to the ones as described in the known literature references (for example, refer to the Official Gazettes of JP-A Nos. Sho 55-59136 and Sho 55-59136), 2,3-pyrazinedicarboxylic acid derivatives represented by the general formula (II-4) can be fluorinated to produce trifluoromethylpyrazinecarboxylic acid derivatives represented by the general formula (II'-1).

Reference Preparation Procedure 7:

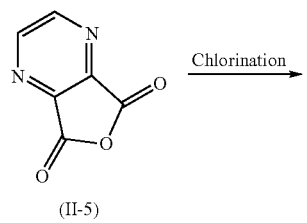

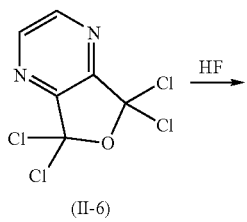

In accordance with a procedure similar to the ones as described in the known literature references (for example, refer to the Official Gazette of JP-A No. Hei 8-81456), 2,3-pyrazinedicarboxylic acid anhydride represented by the general formula (II-5) can be chlorinated to give its chlorinated derivative represented by the general formula (II-6), followed by reaction with hydrogen fluoride by a procedure similar to the ones described in the known literature references (for example, refer to Chemical Abstracts (AN: 1963: 475140), an English excerpt from Zhurnal Obshchei Chimii) to produce a trifluoromethylpyrazinecarboxylic acid derivative represented by the general formula (II'-1).

Reference Preparation Procedure 8:

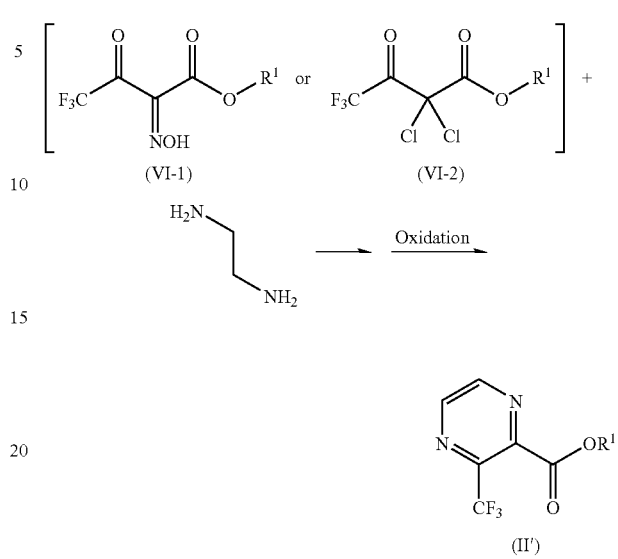

In accordance with a procedure similar to the ones described in the known literature references (for example, refer to J. Org. Chem., 45, 161 (1980), J. Org. Chem., 45, 163 (1980) and Indian J. Org. Chem. Sect. B, 23, 850 (1984)), keto esters represented by the general formula (VI-1) or (VI-2) can be reacted with ethylenediamine to allow cyclization, followed by oxidation to produce trifluoromethylpyrazine-carboxylic acid derivatives represented by the general formula (II').

The pyrazinedicarboxylic acid derivative of (II'-2) where X is for example a difluoromethyl group can be produced, for example, in accordance with the procedure as described in the below Reference Preparation Procedure 9, etc.

Reference Preparation Procedure 9:

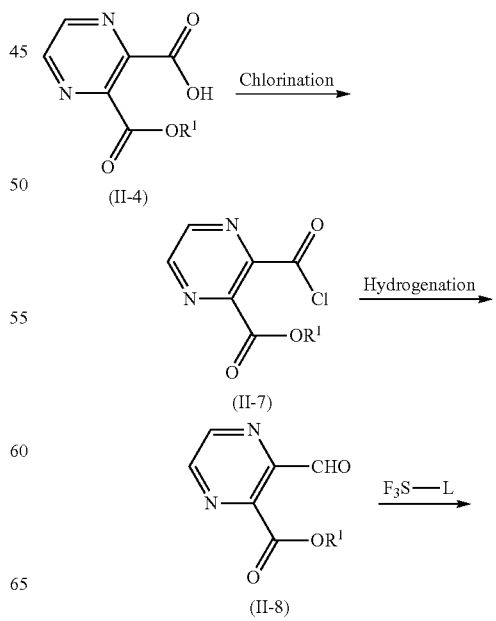

-continued

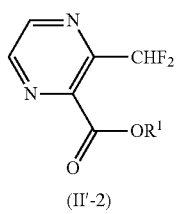

(II'-2)

(wherein $R^1$ is as defined above; L is —$N(CH_3)_2$, —$N(C_2H_5)_2$, —$N(CH_2CH_2OCH_3)_2$, or —$N(CH_2CH_2)_2O$).

In accordance with a procedure similar to the ones described in the known literature references (for example, refer to the Official Gazette of Japanese Translation of PCT Application No. 2004-528297), 2,3-pyrazinedicarboxylic acid derivatives represented by the general formula (II-4) can be converted to their aldehyde derivatives represented by the general formula (II-8) via their acid halides represented by the general formula (II-7), followed by fluorination of their formyl groups with known fluorinating agents (for example, refer to J. Org. Chem., 64, 7048 (1999)) to produce difluoromethylpyrazinecarboxylic acid derivatives represented by the general formula (II'-2).

2-Aminobiphenyl derivatives represented by the general formula (III) can be produced by the procedures as described in Tetrahedron Letters, vol. 28, 5093 (1987) and Tetrahedron Letters, vol. 90, 5436 (1988), etc. or procedures similar thereto.

Production Process 2:

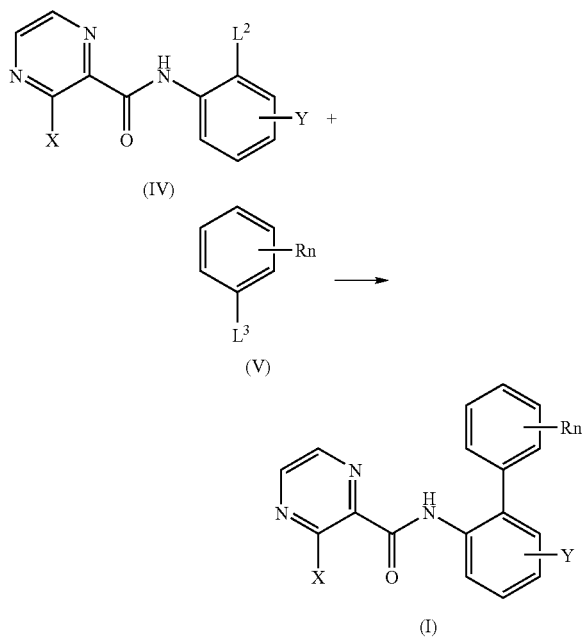

[wherein X, Y, R and n are as defined above; $L^2$ is a leaving group, such as chlorine, bromine and iodine atoms, a trifluoro-methanesulfonyl group, etc.; $L^3$ is a $B(OH)_2$, $B(OR^2)_2$ (where $R^2$ may be the same or different, and represents a $(C_1-C_{10})$alkyl group, or two $R^2$s may combine at their terminals to form a —$CH_2CH_2$— or —$C(CH_3)_2C(CH_3)_2$— group) or $Sn(R^3)_3$ (where $R^3$ may be the same or different and represents a $(C_1-C_{10})$alkyl group) group].

A pyrazinecarboxamide derivative represented by the general formula (IV) and a compound represented by the general formula (V) can be reacted in an inert solvent in the presence of a catalyst and a base to produce a pyrazinecarboxamide derivative of the present invention as represented by the general formula (I). This reaction is normally carried out at a reaction temperature in the range of about 20° C. to 150° C. for a reaction time in the range of 1 hour to 24 hours. A compound represented by the general formula (V) is normally used in proportions of about 0.8 to 5 moles per mole of a pyrazine-Carboxylic acid derivative represented by the general formula (IV).

The catalyst includes, for example, palladium catalysts, such as palladium(II)acetate, tetrakis(triphenyl-phosphine) palladium (0), [1,1'-bis(diphenylphosphino)-ferrocene] dichloropalladium (II) methylene-chloride complex, bis (triphenylphosphine)palladium(II)dichloride, etc. The catalyst is used in proportions in the range of about 0.001 to 0.1 mole per mole of a compound represented by the general formula (V). The base includes, for example, inorganic bases, such as sodium hydroxide, potassium hydroxide, sodium carbonate, potassium carbonate, cesium carbonate, sodium hydrogen carbonate, etc., and acetic acid salts, such as sodium acetate, potassium acetate, etc. The base is normally used in proportions in the range of about 0.5 to 10 moles against each mole of a pyrazinecarbonxylic acid derivative represented by the general formula (IV).

This reaction can be carried out in the presence of a phase-transfer catalyst (which includes, for example, quaternary ammonium salts, such as tetrabutylammonium bromide, benzyltriethylammonium bromide, etc.), as the case may be. In the case of the compound represented by the general formula (V) where $L^3$ is $Sn(R)_3$, furthermore, the reaction can be carried out, for example, in the presence of copper (II) oxide, silver (II) oxide, etc. in order to conduct the reaction efficiently. The inert solvent which can be used may be any inert solvents, unless they hinder or inhibit markedly this reaction, and may be exemplified by alcohols, such as methanol, ethanol, propanol, butanol, 2-propanol, etc., straight-chain or cyclic ethers, such as diethyl ether, tetrahydrofuran, dioxane, etc., aromatic hydrocarbons, such as benzene, toluene, xylene, etc., halogenated hydrocarbons, such as methylene chloride, chloroform, carbon tetrachloride, etc., nitriles, such as acetonitrile, etc., esters, such as ethyl acetate, etc., polar organic solvents, such as N,N-dimethylformamide, N,N-dimethylacetamide, dimethyl sulfoxide, 1,3-dimethyl-2-imidazolinone, water, acetic acid, etc., and the like. These inert solvents can be used solely or as a mixture of not less than two thereof. After completion of the reaction, the objective compound may be isolated from the reaction mixture containing the objective compound by the conventionally employed methods, and purification can be effected by recrystallization, column chromatography, etc., as the case may be, to produce the objective compound. The compounds to be produced may in some instances exist in isomers showing different melting points, as is the case with crystal polymorphism, and any of such isomers are included in the present invention.

Representative examples of the pyrazinecarboxamide derivatives of the present invention as represented by the general formula (I), which are obtained in the above-described manner, are being presented in Tables 1 to 5, but the present invention is not understood to be limited to them. In these Tables, the typical physical properties are expressed as a melting point (° C.). Table 6 tabulates the $^1$HNMR data for the compounds being described as "Amorphous", and in Tables 1 to 5, the compounds showing two different melting points indicated is intended to imply the existence of crystal polymorphism consisting of at least two crystal forms. In the below-shown Tables 1 to 5, "Me" stands for a methyl group, "Et" for an ethyl group, "Pr" for a propyl group, "Bu" for a butyl group, "Ph" for a phenyl group, "n-" for normal, "i-" for iso, and "t-" for tertiary, respectively. And Q1 and Q2 represent the below-illustrated structural formulae, respectively.

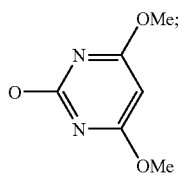

Q1

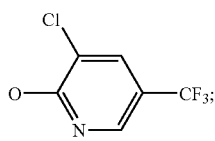

Q2

The general formula (I):

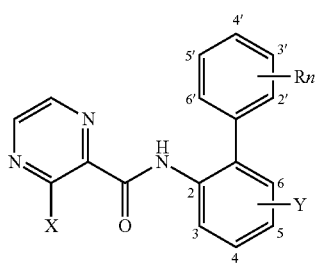

(I)

TABLE 1

(X = Cl)

| Compound Nos. | Y | Rn | Typical physical properties |
|---|---|---|---|
| 1-1 | H | 2'-F | |
| 1-2 | H | 3'-F | |
| 1-3 | H | 3'-Cl | 121-122 |
| 1-4 | H | 3'-CF$_3$ | 115-117 |
| 1-5 | H | 4'-F | 107.6-109 |
| 1-6 | H | 4'-Cl | 130-133 |
| 1-7 | H | 4'-Br | 148-149 |
| 1-8 | H | 4'-Me | 111-113 |
| 1-9 | H | 4'-Et | |
| 1-10 | H | 4'-t-Bu | 115.5-116.5 |
| 1-11 | H | 4'-CF$_3$ | 154.7-155.6 |
| 1-12 | H | 4'-OMe | |
| 1-13 | H | 4'-OCHF$_2$ | |
| 1-14 | H | 4'-OCF$_3$ | 89-94 |
| 1-15 | H | 4'-SMe | 116.6-117.5 |
| 1-16 | H | 4'-SO$_2$Me | |
| 1-17 | H | 4'-CN | 201-204 |
| 1-18 | H | 4'-C(Me)=NOMe | 124-125 |
| 1-19 | H | 4'-C(Me)=NOPr-n | |
| 1-20 | H | 4'-C(Me)=NOPr-i | |
| 1-21 | H | 3',4'-F$_2$ | 141.7-142.9 |
| 1-22 | H | 3',4'-Cl$_2$ | 153.7-155 |
| 1-23 | H | 3'-F-4'-Cl | |
| 1-24 | H | 3'-Cl-4'-F | |
| 1-25 | H | 3'-Me-4'-F | |
| 1-26 | H | 3'-Me-4'-Cl | |
| 1-27 | H | 3'-Cl-4'-Me | |
| 1-28 | H | 3'-Cl-4'-CF$_3$ | Amorphous |
| 1-29 | H | 3'-CF$_3$-4'-Cl | |

TABLE 1-continued (X = Cl)

| Compound Nos. | Y | Rn | Typical physical properties |
|---|---|---|---|
| 1-30 | H | 3'-OCH$_2$O-4' | |
| 1-31 | H | 3'-OCF$_2$O-4' | Amorphous |
| 1-32 | H | 3'-OCF$_2$CF$_2$O-4' | |
| 1-33 | H | 3',5'-F$_2$ | 199-200 |
| 1-34 | H | 3',5'-Cl$_2$ | 167-168 |
| 1-35 | H | 3',5'-(CF$_3$)$_2$ | 152-153 |
| 1-36 | H | 2'-F-4'-Cl | 147-151 |
| 1-37 | H | 3'-Cl-4'-CO$_2$Et | 83-86 |
| 1-38 | H | 2'-Me-4'-OCF$_3$ | 94.5-95.5 |
| 1-39 | H | 2'-,4'-F$_2$ | 103.5-105 |
| 1-40 | H | 2',4'-Cl$_2$ | 157-158 |
| 1-41 | H | 2',5'-F$_2$ | |
| 1-42 | H | 2',3'-F$_2$ | |
| 1-43 | H | 4'-Ph(4''-Br) | |
| 1-44 | H | 4'-OPh | 100-106 |
| 1-45 | H | 4'-OPh(4''-Cl) | |
| 1-46 | H | 4'-Q1 | 137-143 |
| 1-47 | H | 4'-Q2 | 79-80 |
| 1-48 | H | 3'-Q2 | |
| 1-49 | 5-Me | 4'-Cl | |
| 1-50 | 4-F | 4'-Cl | |
| 1-51 | H | 2'-Me-4'-Cl | |
| 1-52 | H | 2'-Me-4'-F | |
| 1-53 | H | 2'-Me-3',4'-Cl$_2$ | |
| 1-54 | H | 2'-Me-3',4'-F$_2$ | |
| 1-55 | H | 2'-F-4',5'-Cl$_2$ | |
| 1-56 | H | 2',4',5'-F$_3$ | |
| 1-57 | H | 2',5'-F$_2$-4'-Cl | |
| 1-58 | H | 3',5'-Cl$_2$-4'-Me | |
| 1-59 | H | 3',5'-F$_2$-4'-Me | |

TABLE 2

(X = Me)

| Compound Nos. | Y | Rn | Typical physical properties |
|---|---|---|---|
| 2-1 | H | 2'-F | |
| 2-2 | H | 3'-F | |
| 2-3 | H | 3'-Cl | |
| 2-4 | H | 3'-CF$_3$ | |
| 2-5 | H | 4'-F | 163.6-165 |
| 2-6 | H | 4'-Cl | 146-147 |
| 2-7 | H | 4'-Br | 125-126 |
| 2-8 | H | 4'-Me | 127-128 |
| 2-9 | H | 4'-Et | |
| 2-10 | H | 4'-t-Bu | |
| 2-11 | H | 4'-CF$_3$ | 143.9-144.3 |
| 2-12 | H | 4'-OMe | Amorphous |
| 2-13 | H | 4'-OCHF$_2$ | |
| 2-14 | H | 4'-OCF$_3$ | 120-121 |
| 2-15 | H | 4'-SMe | |
| 2-16 | H | 4'-SO$_2$Me | |
| 2-17 | H | 4'-CN | |
| 2-18 | H | 4'-C(Me)=NOMe | |
| 2-19 | H | 4'-C(Me)=NOPr-n | |
| 2-20 | H | 4'-C(Me)=NOPr-i | |
| 2-21 | H | 3',4'-F$_2$ | 173-174 |
| 2-22 | H | 3',4'-Cl$_2$ | 178.4-179 |
| 2-23 | H | 3'-F-4'-Cl | |
| 2-24 | H | 3'-Cl-4'-F | |
| 2-25 | H | 3'-Me-4'-F | |
| 2-26 | H | 3'-Me-4'-Cl | |
| 2-27 | H | 3'-Cl-4'-Me | |
| 2-28 | H | 3'-Cl-4'-CF$_3$ | |
| 2-29 | H | 3'-CF$_3$-4'-Cl | |
| 2-30 | H | 3'-OCH$_2$O-4' | |
| 2-31 | H | 3'-OCF$_2$O-4' | |
| 2-32 | H | 3'-OCF$_2$CF$_2$O-4' | |
| 2-33 | H | 3',5'-F$_2$ | |
| 2-34 | H | 3',5'-Cl$_2$ | |

TABLE 2-continued (X = Me)

| Compound Nos. | Y | Rn | Typical physical properties |
|---|---|---|---|
| 2-35 | H | 3',5'-(CF$_3$)$_2$ | |
| 2-36 | H | 2'-F-4'-Cl | 107-108 |
| 2-37 | H | 3'-Cl-4'-CO$_2$Et | 138-139 |
| 2-38 | H | 2'-Me-4'-OCF$_3$ | 53-55 |
| 2-39 | H | 2',4'-F$_2$ | |
| 2-40 | H | 2',4'-Cl$_2$ | 93-96 |
| 2-41 | H | 2',5'-F$_2$ | |
| 2-42 | H | 2',3'-F$_2$ | |
| 2-43 | H | 4'-Ph(4"-Br) | |
| 2-44 | H | 4'-OPh | |
| 2-45 | H | 4'-OPh(4"-Cl) | |
| 2-46 | H | 4'-Q1 | |
| 2-47 | H | 4'-Q2 | |
| 2-48 | H | 3'-Q2 | |
| 2-49 | 5-F | 4'-Cl | |
| 2-50 | 4-F | 4'-Cl | |
| 2-51 | H | 2'-Me-4'-Cl | |
| 2-52 | H | 2'-Me-4'-F | |
| 2-53 | H | 2'-Me-3',4'-Cl$_2$ | |
| 2-54 | H | 2'-Me-3',4'-F$_2$ | |
| 2-55 | H | 2'-F-4',5'-Cl$_2$ | |
| 2-56 | H | 2',4',5'-F$_3$ | |
| 2-57 | H | 2',5'-F$_2$-4'-Cl | |
| 2-58 | H | 3',5'-Cl$_2$-4'-Me | |
| 2-59 | H | 3',5'-F$_2$-4'-Me | |

TABLE 3

(X = CF$_3$)

| Compound Nos. | Y | Rn | Typical physical properties |
|---|---|---|---|
| 3-1 | H | 2'-F | |
| 3-2 | H | 3'-F | |
| 3-3 | H | 3'-Cl | 110.5-111.5 |
| 3-4 | H | 3'-CF$_3$ | 120-121.5 |
| 3-5 | H | 4'-F | 133-134 |
| 3-6 | H | 4'-Cl | 144-145 |
| 3-7 | H | 4'-Br | 156-157 |
| 3-8 | H | 4'-Me | 110-111 |
| 3-9 | H | 4'-Et | |
| 3-10 | H | 4'-t-Bu | 127.8-129.1 |
| 3-11 | H | 4'-CF$_3$ | 147-148 |
| 3-12 | H | 4'-OMe | |
| 3-13 | H | 4'-OCHF$_2$ | |
| 3-14 | H | 4'-OCF$_3$ | 138-140 |
| 3-15 | H | 4'-Sme | 121.5-122.5 |
| 3-16 | H | 4'-SO$_2$Me | |
| 3-17 | H | 4'-CN | |
| 3-18 | H | 4'-C(Me)=NOMe | 132-133 |
| 3-19 | H | 4'-C(Me)=NOPr-n | |
| 3-20 | H | 4'-C(Me)=NOPr-i | |
| 3-21 | H | 3',4'-F$_2$ | 116-117 |
| 3-22 | H | 3',4'-Cl$_2$ | 111.5-112.1 131-132 (Crystal polymorphism) |
| 3-23 | H | 3'-F-4'-Cl | 127-128 |
| 3-24 | H | 3'-Cl-4'-F | 128-129 |
| 3-25 | H | 3'-Me-4'-F | 94-95 |
| 3-26 | H | 3'-Me-4'-Cl | 140-141 |
| 3-27 | H | 3'-Cl-4'-Me | 104-105 |
| 3-28 | H | 3'-Cl-4'-CF$_3$ | 126-130 |
| 3-29 | H | 3'-CF$_3$-4'-Cl | 144-147 |
| 3-30 | H | 3'-OCH$_2$O-4' | |
| 3-31 | H | 3'-OCF$_2$O-4' | 122-123 |
| 3-32 | H | 3'-OCF$_2$CF$_2$O-4' | |
| 3-33 | H | 3',5'-F$_2$ | 119-120 |
| 3-34 | H | 3',5'-Cl$_2$ | 117-118 |
| 3-35 | H | 3',5'-(CF$_3$)$_2$ | 147-148 |
| 3-36 | H | 2'-F-4'-Cl | 137-138 |

TABLE 3-continued (X = CF$_3$)

| Compound Nos. | Y | Rn | Typical physical properties |
|---|---|---|---|
| 3-37 | H | 3'-Cl-4'-CO$_2$Et | 83.5-84.5 |
| 3-38 | H | 2'-Me-4'-OCF$_3$ | 76-77 |
| 3-39 | H | 2',4'-F$_2$ | 117-118 |
| 3-40 | H | 2',4'-Cl$_2$ | 135.5-136.5 |
| 3-41 | H | 2',5'-F$_2$ | 88-89 |
| 3-42 | H | 2',3'-F$_2$ | Amorphous |
| 3-43 | H | 4'-Ph(4"-Br) | 160-163 |
| 3-44 | H | 4'-OPh | 152-153 |
| 3-45 | H | 4'-Oph(4"-Cl) | |
| 3-46 | H | 4'-Q1 | 167-168 |
| 3-47 | H | 4'-Q2 | 143-144 |
| 3-48 | H | 3'-Q2 | |
| 3-49 | 5-Cl | 4'-Cl | |
| 3-50 | 4-F | 4'-Cl | |
| 3-51 | H | 2'-Me-4'-Cl | 112 |
| 3-52 | H | 2'-Me-4'-F | 116 |
| 3-53 | H | 2'-Me-3',4'-Cl$_2$ | |
| 3-54 | H | 2'-Me-3',4'-F$_2$ | |
| 3-55 | H | 2'-F-4',5'-Cl$_2$ | |
| 3-56 | H | 2',4',5'-F$_3$ | |
| 3-57 | H | 2',5'-F$_2$-4'-Cl | |
| 3-58 | H | 3',5'-Cl$_2$-4'-Me | |
| 3-59 | H | 3',5'-F$_2$-4'-Me | |
| 3-60 | H | 2'-Me-5'-F | |
| 3-61 | H | 3'-F-4-Me | 92-93 |
| 3-62 | H | 2'-Me-5'-F | |
| 3-63 | H | 3'-F-4'-CHF2 | 111 |
| 3-64 | H | 3'-CHF2-4-F | 130-131 |
| 3-65 | H | 3'-Cl-4'-CHF2 | 128 |
| 3-66 | H | 3'-F-4'-CF3 | |
| 3-67 | H | 2'-CHF2-4'-F | |
| 3-68 | H | 2'-CHF2-4'-Cl | |
| 3-69 | H | 3'-F-4'-OCF3 | 103-104 |
| 3-70 | H | 3'-F-4'-OCHF2 | 95-100 |
| 3-71 | H | 3'-Cl-4'-OCHF2 | Amorphous |
| 3-72 | H | 3'-OCHF2-4'-Cl | |
| 3-73 | H | 3'-OCHF2-4'-F | |
| 3-74 | H | 3',5'-(Me)2-4'-Cl | 122.5-123.5 |
| 3-75 | H | 3',5'-(Me)2-4'-F | Amorphous |
| 3-76 | H | 3',5'-F2-4'-Cl | 128.5-129.5 |
| 3-77 | H | 3',4',5'-F3 | 145 |
| 3-78 | H | 3',5'-F2-4'-OCHF2 | |
| 3-79 | H | 3'-5'-F2-4'-CO2Et | |
| 3-80 | H | 3'-Cl-4'-OCHF2-5'-F | |
| 3-81 | H | 3'-F-4'-OC(CO2Et)=CH-5' | |
| 3-82 | H | 3'-F-4'-OCH=CH-5' | |
| 3-83 | H | 4'-C≡CC(Me)3 | |
| 3-84 | H | 4'-C≡CC(Me)2OH | |
| 3-85 | H | 3'-F-4'-C≡CC(Me)3 | |
| 3-86 | 4-F | 3',4'-Cl2 | |
| 3-87 | 4-F | 3',4'-F2 | |
| 3-88 | 4-F | 3'-F-4'-Cl | |
| 3-89 | 4-F | 4'-C(Me)=NOMe | |

TABLE 4

(X = CHF$_2$)

| Compound Nos. | Y | Rn | Typical physical properties |
|---|---|---|---|
| 4-1 | H | 2'-F | |
| 4-2 | H | 3'-F | |
| 4-3 | H | 3'-Cl | |
| 4-4 | H | 3'-CF$_3$ | |
| 4-5 | H | 4'-F | |
| 4-6 | H | 4'-Cl | Amorphous |
| 4-7 | H | 4'-Br | |
| 4-8 | H | 4'-Me | |
| 4-9 | H | 4'-Et | |
| 4-10 | H | 4'-t-Bu | |
| 4-11 | H | 4'-CF$_3$ | |

TABLE 4-continued (X = CHF$_2$)

| Compound Nos. | Y | Rn | Typical physical properties |
|---|---|---|---|
| 4-12 | H | 4'-OMe | |
| 4-13 | H | 4'-OCHF$_2$ | |
| 4-14 | H | 4'-OCF$_3$ | |
| 4-15 | H | 4'-Sme | |
| 4-16 | H | 4'-SO$_2$Me | |
| 4-17 | H | 4'-CN | |
| 4-18 | H | 4'-C(Me)=NOMe | |
| 4-19 | H | 4'-C(Me)=NOPr-n | |
| 4-20 | H | 4'-C(Me)=NOPr-i | |
| 4-21 | H | 3',4'-F$_2$ | Amorphous |
| 4-22 | H | 3',4'-Cl$_2$ | Amorphous |
| 4-23 | H | 3',-F-4'-Cl | |
| 4-24 | H | 3'-Cl-4'-F | |
| 4-25 | H | 3'-Me-4'-F | |
| 4-26 | H | 3'-Me-4'-Cl | |
| 4-27 | H | 3'-Cl-4'-Me | |
| 4-28 | H | 3'-Cl-4'-CF$_3$ | |
| 4-29 | H | 3'-CF$_3$-4'-Cl | |
| 4-30 | H | 3'-OCH$_2$O-4' | |
| 4-31 | H | 3'-OCF$_2$O-4' | |
| 4-32 | H | 3'-OCF$_2$CF$_2$O-4' | |
| 4-33 | H | 3',5'-F$_2$ | |
| 4-34 | H | 3',5'-Cl$_2$ | |
| 4-35 | H | 3',5'-(CF$_3$)$_2$ | |
| 4-36 | H | 2'-F-4'-Cl | |
| 4-37 | H | 3'-Cl-4'-CO$_2$Et | |
| 4-38 | H | 2'-Me-4'-OCF$_3$ | |
| 4-39 | H | 2',4'-F$_2$ | |
| 4-40 | H | 2',4'-Cl$_2$ | |
| 4-41 | H | 2',5'-F$_2$ | |
| 4-42 | H | 2',3'-F$_2$ | |
| 4-43 | H | 4'-Ph(4''-Br) | |
| 4-44 | H | 4'-OPh | |
| 4-45 | H | 4'-Oph(4''-Cl) | |
| 4-46 | H | 4'-Q1 | |
| 4-47 | H | 4'-Q2 | |
| 4-48 | H | 3'-Q2 | |
| 4-49 | 5-Cl | 4'-Cl | |
| 4-50 | 4-F | 4'-Cl | |
| 4-51 | H | 2'-Me-4'-Cl | |
| 4-52 | H | 2'-Me-4'-F | |
| 4-53 | H | 2'-Me-3',4'-Cl$_2$ | |
| 4-54 | H | 2'-Me-3',4'-F$_2$ | |
| 4-55 | H | 2'-F-4',5'-Cl$_2$ | |
| 4-56 | H | 2',4',5'-F$_3$ | |
| 4-57 | H | 2',5'-F$_2$-4'-Cl | |
| 4-58 | H | 3',5'-Cl$_2$-4'-Me | |
| 4-59 | H | 3',5'-F$_2$-4'-Me | |

TABLE 5

(X = CH$_2$F)

| Compound Nos. | Y | Rn | Typical physical properties |
|---|---|---|---|
| 5-1 | H | 2'-F | |
| 5-2 | H | 3'-F | |
| 5-3 | H | 3'-Cl | |
| 5-4 | H | 3'-CF$_3$ | |
| 5-5 | H | 4'-F | |
| 5-6 | H | 4'-Cl | |
| 5-7 | H | 4'-Br | |
| 5-8 | H | 4'-Me | |
| 5-9 | H | 4'-Et | |
| 5-10 | H | 4'-t-Bu | |
| 5-11 | H | 4'-CF$_3$ | |
| 5-12 | H | 4'-Ome | |
| 5-13 | H | 4'-OCHF$_2$ | |
| 5-14 | H | 4'-OCF$_3$ | |
| 5-15 | H | 4'-Sme | |
| 5-16 | H | 4'-SO$_2$Me | |
| 5-17 | H | 4'-CN | |
| 5-18 | H | 4'-C(Me)=NOMe | |
| 5-19 | H | 4'-C(Me)=NOPr-n | |
| 5-20 | H | 4'-C(Me)=NOPr-i | |
| 5-21 | H | 3',4'-F$_2$ | |
| 5-22 | H | 3',4'-Cl$_2$ | |
| 5-23 | H | 3'-F-4'-Cl | |
| 5-24 | H | 3'-Cl-4'-F | |
| 5-25 | H | 3'-Me-4'-F | |
| 5-26 | H | 3'-Me-4'-Cl | |
| 5-27 | H | 3'-Cl-4'-Me | |
| 5-28 | H | 3'-Cl-4'-CF$_3$ | |
| 5-29 | H | 3'-CF$_3$-4'-Cl | |
| 5-30 | H | 3'-OCH$_2$O-4' | |
| 5-31 | H | 3'-OCF$_2$O-4' | |
| 5-32 | H | 3'-OCF$_2$CF$_2$O-4' | |
| 5-33 | H | 3',5'-F$_2$ | |
| 5-34 | H | 3',5'-Cl$_2$ | |
| 5-35 | H | 3',5'-(CF$_3$)$_2$ | |
| 5-36 | H | 2'-F-4'-Cl | |
| 5-37 | H | 3'-Cl-4'-CO$_2$Et | |
| 5-38 | H | 2'-Me-4'-OCF$_3$ | |
| 5-39 | H | 2',4'-F$_2$ | |
| 5-40 | H | 2',4'-Cl$_2$ | |
| 5-41 | H | 2',5'-F$_2$ | |
| 5-42 | H | 2',3'-F$_2$ | |
| 5-43 | H | 4'-Ph(4''-Br) | |
| 5-44 | H | 4'-OPh | |
| 5-45 | H | 4'-Oph(4''-Cl) | |
| 5-46 | H | 4'-Q1 | |
| 5-47 | H | 4'-Q2 | |
| 5-48 | H | 3'-Q2 | |
| 5-49 | 5-Cl | 4'-Cl | |
| 5-50 | 4-F | 4'-Cl | |
| 5-51 | H | 2'-Me-4'-Cl | |
| 5-52 | H | 2'-Me-4'-F | |
| 5-53 | H | 2'-Me-3',4'-Cl$_2$ | |
| 5-54 | H | 2'-Me-3',4'-F$_2$ | |
| 5-55 | H | 2'-F-4',5'-Cl$_2$ | |
| 5-56 | H | 2',4',5'-F$_3$ | |
| 5-57 | H | 2',5'-F$_2$-4'-Cl | |
| 5-58 | H | 3',5'-Cl$_2$-4'-Me | |
| 5-59 | H | 3',5'-F$_2$-4'-Me | |

TABLE 6

| Compound Nos. | $^1$H-NMR (CDCl$_3$/TMS, δ value ppm) |
|---|---|
| 1-31 | 7.15-7.30 (m, 5H), 7.40-7.60 (m, 2H), 8.35 (d, 1H), 8.60 (d, 1H), 9.70 (br.s, 1H) |
| 3-42 | 7.10-7.20 (m, 2H), 7.25-7.40 (m, 3H), 7.52 (t, 1H), 8.45 (d, 1H), 8.60 (d, 1H), 8.80 (d, 1H), 9.48 (br.s, 1H) |
| 3-71 | 6.64 (t, 1H), 7.26-7.40 (m, 4H), 7.48 (t, 1H), 7.60 (d, 1H), 8.53 (d, 1H), 8.62 (d, 1H), 8.82 (d, 1H), 9.60 (br, 1H) |

The pyrazinecarboxamide derivatives of the present invention as represented by the general formula [I] or their salts possess the controlling effect against plant diseases. Consequently, the pyrazinecarboxamide derivatives of the present invention as represented by the general formula [I] or their salts can find application especially as a plant disease controlling agent for agricultural and horticultural uses. On the basis of this, the present invention also provides a method for controlling a plant disease which comprises treating plants (especially plants for agricultural and horticultural uses) with the above-mentioned pyrazinecarboxamide derivatives represented by the general formula [I] or their salts. And the "treatment", which is to be effected with the above-described pyrazinecarboxamide derivatives of the present invention as represented by the general formula [I] or their salts, includes the spraying or spreading of the above-described chemical substances onto the targeted plant, as well as the spraying or drenching thereof onto the soil where the targeted plant is grown, and the like.

The plant disease controlling agent for agricultural and horticultural uses, which contains a pyrazinecarboxamide derivative of the present invention as represented by the general formula [I] or its salts, is particularly suited for the control of plant diseases of rice plants, fruit trees, vegetables and miscellaneous crop plants, as well as flowers and ornamental plants.

The targeted diseases, against which the plant disease controlling agent of the present invention is to be used, include, for example, diseases caused by fungi or molds, diseases caused by bacteria, diseases caused by viruses, and the like. The diseases caused by molds are exemplified by the diseases caused by the Fungi Imperfecti family (for example, the diseases caused by the *Botrytis* genus, the *Helminthsporium* genus, the *Fusarium* genus, the *Septoria* genus, the *Cercospora* genus, the *Pseudocercosporella* genus, the *Rhynchosporium* genus, the *Pyricularia* genus, the *Alternaria* genus, and the like), the diseases caused by the Basidomycetes family (for example, the diseases caused by the *Hemilelia* genus, the *Rhizoctonia* genus, the *Ustilago* genus, the *Typhula* genus, the *Puccinia* genus, and the like), the diseases caused by the Ascomycetes family (for example, the diseases caused by the *Venturia* genus, the *Podosphaera* genus, the *Leptosphaeria* genus, the *Blumeria* genus, the *Erypsia* genus, the *Microdochium* genus, *Sclerotinia* genus, the *Gaeumannomyces* genus, the *Monilinia* genus, the *Unsinula* genus, and the like), the diseases caused by miscellaneous families of fungi (for example, the diseases caused by the *Ascochyta* genus, the *Phoma* genus, the *Pythium* genus, the *Corticium* genus, the *Pyrenophora* genus, and the like), and the like. The diseases caused by bacteria include, for example, the diseases caused by the *Pseudomonas* genus, the *Xanthomonas* genus, the *Erwinia* genus, and the like, and the diseases caused by viruses include, for example, the diseases caused by the tobacco mosaic virus, etc.

As the particular or specific examples of the diseases caused by fungi, there may be mentioned blast of rice plant (caused by *Pyricularia oryzae*), sheath blight of rice plant (caused by *Rhizoctonia solani*), stripe of rice plant (caused by *Cochiobolus miyabeanus*), seedling blight of rice plant (caused by *Rhizopus chinensis, Pythium graminicola, Fusarium graminicola, Fusarium roseum, Mucro* sp., *Phoma* sp., *Tricoderma* sp.), "bakanae" disease of rice plant (caused by *Gibberella fujikuroi*), powdery mildew of barley and wheat plants (caused by *Blumeria graminis*), powdery mildew of cucumber plant, etc. (caused by *Sphaerotheca fuliginea*), powdery mildew of eggplant plant, etc. (caused by *Erysiphe cichoracoarum*) and powdery mildews of miscellaneous host plants, eye spot of barley and wheat plants (caused by *Pseudocercosporella herpotrichoides*), smuts of wheat plant, etc. (caused by *Urocystis tritici*), snow blight of barley and wheat plants, etc. (caused by *Microdochium nivalis, Pythium iwayamai, Typhla ishikariensis, Typhla incarnate, Sclerotinia borealis*), scabs of barley and wheat plants, etc. (caused by *Fusarium graminearum, Fusarium avenaceum, Fusarium culmorum, Microdochium nivalis*), rusts of barley and wheat plants, etc. (caused by *Puccinia recondite, Puccinia striiformis, Puccinia graminis*), take-alls of barley and wheat plants, etc. (caused by *Gaeumannomyces graminis*), crown rust of oat plant (caused by *Pucinia coronata*), and rusts of mecellaneous plants, gray molds of cucumber and strawberry plants, etc. (caused by *Botrytis cinerea*), stem rots of tomato and cabbage plants, etc. (caused by *Sclerotinia sclerotiorum*), late blights of potato and tomato plants, etc. (caused by *Phytophthora infestans*) and miscellaneous plants, rusts of various plants, such as downy mildew of cucumber plant (caused by *Pseudoperonospora cubensis*), downy mildew of grape tree, etc., scab of apple tree (caused by *Venturia inaequalis*), leaf spot of apple tree (caused by *Alternaria mali*), black spot of Japanese pear tree (caused by *Alternaria kikuchiana*), stem end rot of citrus fruit trees (caused by *Diaporthe citri*), scab of citrus fruit trees (caused by *Elsinoe fawcetti*), brown leaf spot of beat plant (caused by *Cercospora beticola*), brown leaf spot of peanut plant (caused by *Cercospora arachidicola*), leaf spot of peanut plant (caused by *Cercospora personata*), speckled leaf blotch of wheat plant (caused by *Septoria tritici*), glume blotch of wheat plant (caused by *Leptosphaeria nodorum*), rot blotch of barley plant (caused by *Pyrenophora teres*), leaf stripe of barley plant (caused by *Pyrenophora graminea*), scald of barley plant (caused by *Rhynchosporium secalis*), loose smut of wheat plant (caused by *Ustilago nuda*), stinking smut of wheat plant (caused by *Tilletia caries*), brown patch of turf or lawn grass (caused by *Rhizoctonia solani*), dollar spot of turf or lawn grass (caused by *Sclerotinia homoeocarpa*), and the like.

As the particular or specific examples of the diseases caused by bacteria, there may be mentioned the diseases caused by the *Pseudomonas* genus, such as bacterial spot blotch of cucumber plant (caused by *Pseudomonas syringae* pv. *lachrymans*), bacterial wilt of tomato plant (caused by *Ralstonia solanacearum*) and bacterial grain rot of rice plant (caused by *Burkholderia glumae*), the diseases caused by the *Xanthomonas* genus, such as black rot of cabbage plant (caused by *Xanthomonas campestris*), bacterial leaf blight of rice plant (caused by *Xanthomonas oryzae*) and cankar of citrus fruit trees (caused by *Xanthomonas citri*), the diseases caused by the *Erwinia* genus, such as bacterial soft rot of cabbage plant (caused by *Erwinia carotovora*), and the like.

The particular or specific disease examples of the diseases caused by viruses include tobacco mosaic (caused by Tobacco mosaic virus), and the like.

The plants to which the plant disease controlling agent of the present invention is applicable are not particularly limited, and include, for example, cereal plants (for example, plants of rice, barley, wheat, rye, oat, corn, sorghum, etc.), bean plants (for example, plants of soybean, small red bean, broad bean, garden pea, peanut, etc.), fruit trees and fruits (for example, trees of apple, citrus fruits, pear, grape, peach, Japanese apricot or plum, cherry, walnuts, almond, banana, strawberry, etc. and their fruits), vegetables (for example, plants of cabbage, tomato, spinach, broccoli, lettuce, onion, Welsh onion, piment, etc.), root vegetables (for example, plants of carrot, potato, sweet potato, Japanese radish, East Indian lotus, turnip, etc.), industrial crops or crops for industrial processing (for example, plants or trees of cotton, hemp, paper mulberry, mitsumata, rape, beet, hop, sugar cane, sugar beet, olive, rubber or gum, coffee, tobacco, tea, etc.), cucurbitaceous vegetables (for example, plants of pumpkin, cucumber, watermelon, melon, etc.), forage grasses (for example, orchard lawn grass, sorghum, timothy, clover, alphalpha, etc.), lawn grass or turf (for example, korai-lawn grass, bent lawn grass, etc.), crops for fragrances, etc. (for example, plants of lavender, rosemary, thyme, parsley, pepper, ginger, etc.), flowers (for example, chrysanthemum, rose, orchid, etc.), and the like.

Also, the plant disease controlling agent of the present invention can find practical application in the IPM (which stands for "integrated pest management"). IPM includes, for example, the introduction of genetically-modified crop (for example, herbicide-resistant crop, pest-resistant crop having been transfected with the gene encoding an insecticidal protein, disease resistant crop having been transfected with the gene encoding a substance capable of inducing resistance to the disease, taste-improving crop, longer-preservable crop producing plants, yield-improved crop, etc.), utilization of pheromone formulations, such as insect-pheromones (for example, communication disturbing agents among moths), practical utilization of natural-enemy insects, etc., practical utilization of chemical-based agrochemicals, and the like. The plant disease controlling agent of the present invention can find efficient, practical utilization as the said agrochemicals.

In cases where the compound of the present invention is used as an active ingredient for plant disease controlling agents, it may be used as such without addition of other ingredients, but is preferably used after being normally processed into an agrochemical formulation form convenient for use in accordance with the conventional agrochemical-formulation processing method.

Namely, a pyrazinecarboxamide derivative represented by the general formula (I) or its salts can be used after being incorporated into a suitable inert carrier as such or together with adjuvants in suitable proportions, as the case may be, followed by dissolution, separation, suspension, mixing, impregnation, adsorption or adhesion for the purpose of processing into a suitable agrochemical formulation form, such as suspension, emulsion, solution, wettable powder, water dispersible granule, granule, powder, tablet, pack formulation, and the like.

The inert carrier which can be used in the present invention may be either solid or liquid ones. The material which may be able to serve a useful purpose as a solid carrier includes, for example, soybean meal, cereal meal, wood meal, bark meal, sawdust, tobacco stalk meal, walnut shell meal, wheat bran, cellulose powder, residue after extraction of plant extracts, synthetic polymers such as crushed synthetic polymers, inorganic mineral powders, such as clays (for example, kaolin, bentonite, acid clay, etc.), talcs (for example, talc, pyrrophilite, etc.), silicas (for example, diatomaceous earth, silica sand, mica, white carbon (finely-powdered water-containing silicon, or finely dispersed synthetic silicic acids which, being also referred to as water-containing silicic acid, in some instances consist mainly of calcium silicate), activated carbon, sulfur-powder, pumice, burnt diatomaceous earth, crushed brick, flyash, sand, calcium carbonate, calcium phosphate, etc., plastic carriers, such as polyethylene, polypropylene, polyvinylidene chloride, etc., chemical fertilizers, such as ammonium sulfate, ammonium phosphate, ammonium nitrate, urea, ammonium chloride, etc., compost, and the like. These can be used singly or as a mixture of not less than two thereof.

The material, which can act as a liquid carrier, includes those possessing the solvent capacity and in addition, is selected from materials which eventually get able to disperse the active ingredients by the aid of adjuvants, although they lack in solvent capacity: its representatives can be exemplified by the below-enumerated carriers, which are used singly or as a mixture of not less than two thereof, and there can be mentioned, for example, water, alcohols (for example, methanol, ethanol, isopropanol, butanol, ethylene glycol, etc.), ketones (for example, acetone, methyl ethyl ketone, methyl isobutyl ketone, diisobutyl ketone, cyclohexanone, etc.), ethers (for example, ethyl ether, dioxane, cellosolve, dipropyl ether, tetrahydrofuran, etc.), aliphatic hydrocarbons (for example, kerosene, mineral oil, etc.), aromatic hydrocarbons (for example, benzene, toluene, xylene, solvent naphtha, alkylnaphthalene, etc.), halogenated hydrocarbons (for example, dichloroethane, chloroform, carbon tetrachloride, chlorinated benzenes, etc.), esters (for example, ethyl acetate, diisopropyl phthalate, dibutyl phthalate, dioctyl phthalate, etc.), amides (for example, dimethylformamide, dimethylformamide, dimethylacetamide, etc.), nitriles (for example, acetonitrile, etc.), dimethyl sulfoxide, and the like.

As the adjuvant, there can be mentioned, for example, the below-exemplified surfactants, dispersion stabilizers, tackiness and/or binding adjuvants, flowability improvers, deflocculating agents, antifoaming agents, preservatives, and the like, and these can be suitably used according to the intended object. The adjuvants may be used singly and may in some instances be employed in combination of not less than two thereof, while none of them in some cases needs be used.

The surfactant can be used, for example, for the purposes of emulsification, dispersion, solubilization and/or wetting of the active ingredients, and can be exemplified by polyoxyethylene alkylene ethers, polyoxyethylene polyalkylaryl ethers, polyoxyethylene higher fatty acid esters, polyoxyethylene resin acid esters, polyoxyethylene sorbitan monolaurate, polyoxyethylene sorbitan monooleate, alkylarylsulfonates, naphthalenesulfonate condensates, ligninsulfonates, higher alcohol sulfuric acid esters, and the like.

The dispersion stabilizer and tackiness and/or binding adjuvant can be used for the purpose of stabilization of dispersion of the active ingredients and also as a tackiness and/or binding adjuvant for the formation of particles. And as such dispersion stabilizer and tackiness and/or binding adjuvant, there can be mentioned, for example, casein, gelatin, starch, methylcellulose, carboxymethylcellulose, gum arabic, polyvinyl alcohols, pine root oil, rice bran oil, bentonite, ligninsulfonates, and the like.

The flowability improver can be used for improvement of the flowability of solid agrochemical forms. As the flowability improver, there can be mentioned, for example, wax, stearic acid salts, alkyl phosphates, and the like. The deflocculating agent can be used as a dispersing-deflocculating agent for suspended formulation forms. And as the deflocculating agent, there can be mentioned, for example, naphthalenesulfonate condensates, condensed phosphoric acid salts, and the like.

The antifoaming agent includes, for example, silicone oils, and the like.

The preservative includes, for example, 1,2-benzoisothiazoline-3-on, p-chloro-meta-xylenol, butyl p-oxybenzoate, and the like.

Furthermore, the plant disease controlling agents for agricultural and horticultural uses can be incorporated, as the case may be, with functional spreaders, activity-reinforcing agents, such as metabolic-breakdown inhibitors, for example, piperonyl butoxide, etc., antifreezing agents, such as propylene glycol, etc., antioxidants, such as BHT (dibutylhydroxyltoluene), etc., UV absorbers, miscellaneous additives, and the like.

The formulation proportion of the active ingredient compound, which can be increased or decreased, where necessary, may suitably be selected for utilization from the range of about 0.01 to 90 parts by mass against 100 parts by mass of the plant disease controlling agent for agricultural and horticultural uses, and is appropriately in the range of about 0.01 to 50% by mass in cases where the active ingredient compound is processed for example into an emulsifiable concentrate, wettable powder, dust or granule.

The plant disease controlling agent for agricultural and horticultural uses according to the present invention may be used as such, or in such forms as is suitably diluted or suspended with water, etc. in order to control various diseases.

The plant disease controlling agent for agricultural and horticultural uses according to the present invention is used in such amounts or quantities as may appropriately be selected according to the objective from the range of about 0.001 g to 10 kg per 10 are of the farm surface area, although they vary depending upon a variety of different factors, such as the objective, targeted disease, growing conditions of the crop plant, tendency of occurrence or onset of the disease, weather, ambient conditions, formulation form, and the method, place or time of application, and the like.

The plant disease controlling agent for agricultural and horticultural uses according to the present invention, furthermore with a specific view to enlargement or expansion of the targeted disease pests to be controlled and the optimum controlling time or for the purpose of reduction of the application rates, as the case may be, can be used as a mixture with other pesticides for agricultural and horticultural uses, such as fungicides, insecticides, acaricides, nematicides, biological agrochemicals, and the like, and can also be utilized as a mixture with herbicides, plant growth regulators, fertilizers, and the like, depending upon the application conditions.

The other fungicides for agricultural and horticultural uses to be used for such purposes can be exemplified by sulfur, lime sulfur, basic copper sulfate, iprobenfos, edifenfos, tolclofos-methyl, thiram, polycarbamate, zineb, manzeb, mancozeb, propineb, thiophanate, thiophanate-methyl, benomyl, iminoctadine acetate, iminoctadine-albesilate, mepronil, flutolanil, pencycuron, furametpyr, thifluzamid, metalaxyl, oxadixyl, carpropamid, dichlorfluanid, fulsulfamide, chlorothalonil, cresoxim-methyl, fenoxanil, hymexazole, euclomezole, fluoroimide, procymidone, vinclozolin, iprodione, triadimefon, bitertanol, triflumizole, ipconazole, furconazole, propiconazole, difenoconazole, myclobutanil, tetraconazole, hexaconazole, tebuconazole, tiadinil, imibenconazole, prochloraz, pefurazoate, cyproconazole, isoprothiolane, fenarimol, pyrimetanil, mepanipyrim, pyrifenox, fluazinam, trifoline, diclomezine, azoxystrobin, thiadiazine, captan, probenazole, acibenzolar-S-methyl, fthalide, tricyclazole, pyroquilon, quinomethionate, oxolinic acid, dithianon, kasugamycin, validamycin, polyoxin, blastocidin or streptomycin, and the like.

The insecticides, acaricides and nematicides for agricultural and horticultural uses to be use for the same purpose include, for example, ethion, trichlorfon, methamidphos, acephate, dichlorvos, mevinphos, monocrotophos, malathion, dimethoate, formothion, mecarbam, vamidothion, thiometon, disulfoton, oxydeprofos, naled, methylparathion, fenitrothion, cyanophos, propaphos, fenthion, prothiofos, profenofos, isofenphos, temephos, phenthoate, dimethylvinphos, chlorfenvinphos, tetrachlorvinphos, phoxim, isoxathion, pyraclofos, methidathion, chlorpyrifos, chlorpyrifos-methyl, pyridafenthion, diazinon, pirimiphos-methyl, phosalone, phosmet, dioxabenzofos, quinalphos, terbufos, ethoprophos, cadusafos, mesulfenfos DPS (NK-0795), phosphocarb, fenamiphos, isoamidofos, fosthiazate, isazofos, enaprofos, fenthion, fosthietane, dichlofenthion, thionazin, sulprofos, fensulfothion, diamidafos, pyrethrin, allethrin, prallethrin, resmethrin, permethrin, tefluthrin, bifenthrin, fenpropathrin, cypermethrin, alpha-cypermethrin, cyhalothrin, rhamda-cyhalothrin, delta-methrin, acrinathrin, fenvalerate, esfenvalerate, cycloprothrin, etofenprox, halfenprox, silafluofen, flucythrinate, fluvalinate, methomyl, oxamyl, thiodicarb, aldicarb, alanicarb, cartap, metholcarb, xylicarb, propoxul, fenoxycarb, fenocarb, ethiofencarb, fenothiocarb, bifenazate, BPMC (2-sec-butylphenyl-N-methylcarbamate), carbaryl, pirimicarb, carbofuran, carbosulfan, furathiocarb, benfuracarb, aldoxycarb, diafenthiuron, diflubenzuron, teflubenzuron, hexaflumuron, novaluron, lufenuron, flufenoxuron, chlorfluazuron, fenbutatin oxide, tricyclohexyltin hydroxide, sodium oleate, potassium oleate, methoprene, hydroprene, binapacryl, amitraz, dicofol, kelthane, chlorbenzilate, fenisobromolate, tetradifon, bensultap, benzomate, tebufenozide, methoxyfenozide, pyridalyl, metaflumizone, flubendiamide, chromafenozide, propargite, acequinocyl, endosulfan, diofenolan, chlorphenapyr, fenpyroximate, tolfenpyrad, fipronil, tebufenpyrad, triazamate, ethoxazole, hexythiazox, nicotin-sulfate, nitenpyram, acetamiprid, thiacloprid, imidacloprid, thiamethoxam, clothianidin, dinotefuran, fluazinam, pyriproxyfen, hydramethylnon, pyrimidifen, pyridaben, cyromazine, TPIC (tripropyl isocyanurate), pymetrozine, clofentezine, buprofezin, thiocyclam, fenazaquin, quinomethionate, indoxacarb, polynactin complex, milbemectin, abamectin, emamectin-benzoate, spinosad, BT (*Bacillus thuringiensis*), azadilactin, rotenone, hydroxypropyl-starch, levamisol hydrochloride, metam-sodium, morantel tartrate, dazomet, triclamide, *Bastoria* or *Monacrosporium phymatopagum*, etc.

Similarly, the herbicides include, for example, glyphosate, sulphosate, glufosinate, bialaphos, butamifos, esprocarb, prosulfocarb, benthiocarb, pyributicarb, asulam, linuron, daimuron, isouron, bensulfuron-methyl, cyclosulfamuron, cinosulfuron, pyrazosulfuron-ethyl, azimusulfuron, imazosulfuron, thenylchlor, alachlor, pretilachlor, clomeprop, etobenzanid, mefenacet, pendimethalin, bifenox, acifluofen, lactofen, cyhalofop-butyl, ioxinyl, bromobutide, alloxydim, sethoxydim, napropamide, indanofan, pyrazolate, benzofenap, pyraflfen-ethyl, imzapyr, sulfentrazone, cafenstrole, pentoxazone, oxadiazon, paraquat, diquat, pyriminobac, simazine, atrazine, dimethametryn, triaziflam, benfuresate, fluthiacet-methyl, quizalofop-ethyl, bentazone or calcium peroxide, etc.

Below described are the examples to illustrate the present invention more particularly, but the present invention is not understood to be limited to them, unless they extend over the gist of the present invention.

Example 1

Production of N-(4'-trifluoromethoxybiphenyl-2-yl)-3-methyl-pyrazine-2-carboxamide (Compound No. 2-14)

A solution of sodium carbonate (0.31 g: 1.5 mmole) in 5 mL of water was added to a solution of N-(2-bromophenyl)-3-methylpyrazine-2-carboxamide (0.4 g: 1.4 mmole) and 4-trifluoromethoxyphenyl boric acid (0.31 g: 1.5 mmole) in 10 mL of toluene, followed by addition of tetrakis(triphenyl-Phosphine)palladium (0) (0.1 g: 0.09 mmole). After heating under reflux condition for 6 hours under argon atmosphere, the reaction mixture was cooled to room temperature, and admixed with ethyl acetate and water, followed by separation. The organic layer was washed with water and saturated brine successively, dried over anhydrous sodium sulfate, and concentrated in vacuo. The residue was purified by silica gel column chromatography to give the subject compound (0.35 g).

Yield: 68%

Typical physical properties: melting point of 120 to 121° C.

Example 2

Production of N-(4'-chlorobiphenyl-2-yl)-3-trifluoromethyl-pyrazine-2-carboxamide (Compound No. 3-6)

Triethylamine (0.32 g: 1.5 mmole) was added to a solution of 4'-chlorobiphenyl-2-ylamine (0.3 g: 1.5 mmole) and 3-trifluoromethylpyrazine-2-carboxylic acid chloride (0.32 g: 1.5 mmole) in THF (10 mL), followed by stirring at room temperature for 2 hours. Water was added to the reaction mixture to suspend the reaction, followed by extraction with ethyl acetate. The ethyl acetate layer was dried over anhydrous sodium sulfate and concentrated in vacuo, and the residue was purified by silica gel column chromatography to give the subject compound (0.47 g).

Yield: 85%

Typical physical properties: melting point of 144 to 145° C.

Below described are the representative agrochemical formulations and test examples, but the present invention is not understood to be limited to them.

It meanwhile is added that the term "part" denotes "part by mass".

Agrochemical Formulation Example 1

| | |
|---|---|
| The Compound of the present invention: | 10 parts |
| Xylene: | 70 parts |
| N-Methylpyrrolidone | 10 parts |
| A mixture of polyoxyethylene nonylphenyl ether and calcium alkylbenzenesulfonate | 10 parts |

The above-described ingredients are uniformly mixed and dissolved to make an emulsifiable concentrate.

Agrochemical Formulation Example 2

| | |
|---|---|
| The Compound of the present invention: | 3 parts |
| Clay powder | 82 parts |
| Diatomaceous earth powder | 15 parts |

The above-described ingredients are uniformly blended and finely crushed to make a dust.

Agrochemical Formulation Example 3

| | |
|---|---|
| The Compound of the present invention: | 5 parts |
| A powder mixture of bentonite and clay | 90 parts |
| Calcium liginsulfonate | 5 parts |

The above-described ingredients are uniformly blended and after addition of water, the mixture is kneaded, granulated and dried to make a granule.

Agrochemical Formulation Example 4

| | |
|---|---|
| The Compound of the present invention: | 20 parts |
| Kaolin and synthetic, finely dispersed silicic acid: | 75 parts |
| A mixture of polyoxyethylene nonylphenyl ether and calcium alkylbenzenesulfonate | 5 parts |

The above-described ingredients are uniformly blended and finely crushed to make a wettable powder.

Below described the test examples to demonstrate that the compounds of the present invention are useful as a plant disease controlling agent. It meanwhile is added that in these examples, the compounds of the present invention are expressed as the Compound Number listed in Tables 1 to 5, while the below-shown, three compounds were used as a reference compound to conduct the same evaluation.

Reference Compound A: 3-Methyl-N-(2-methylindan-4-yl)-pyrazine-2-carboxamide (the compound being expressed as Compound No. 13 described in the Official Gazette of JP-A Hei 2-175).

Reference Compound B: N-{3-Isobutyl-4-[1-methoxy-2,2,2-trifluoro-1-(trifluoromethyl)ethyl]phenyl}-3-trifluoromethylpyrazine-2-carboxamide (the compound being expressed as Compound No. 1-43 described in the Pamphlet of WO 05/115994).

Reference Compound C: 2-Chloro-N-(4'-chlorobiphenyl-2-yl)-nicotinamide (the compound being expressed as Compound No. 3-16 described in the Official Gazette of Japanese Patent No. 3202079).

Test Example 1

Test on the Controlling Effect Against Apple Tree Scab

A seedling of an apple tree (the variety: Ohrin) grown in a pot was subjected to foliar application with a diluted emulsion of the emulsifiable concentrate of the compound of the present invention prepared in accordance with Agrochemical Formulation Example 1, which diluted emulsion was produced by diluting the concentrate with water to the specifically determined volume. On the following day after the application, the seedling was inoculated by spraying with a suspension of spores of the causal fungus of apple tree scab (*Venturia inaequalis*) as obtained by culture on the PSA medium (consisting of 1000 mL of a solution obtained by decocting 20 g of sucrose, 15 g of agar and 200 g of potato; as adjusted to pH 7), and maintained at 20° C. under humid conditions. Fourteen days after the inoculation, the fungus protective value (%) was determined in accordance with the equation (1), and the controlling effect was assessed according the below-described criteria of judgment.

Equation (1):

$$\text{Protective value (\%)} = A/B \times 100 \quad (1)$$

where:

A; [(Ratio of the afflicted spotted leaf surface area in non-treated section to the total leaf surface area)−(Ratio of the afflicted spotted leaf surface area in treated section to the total leaf surface area)]

B; (Ratio of the afflicted spotted leaf surface area in non-treated section to the total leaf surface area)
Criteria of Judgment:
0: Less than 9% in protective value
1: 10 to 19% in protective value
2: 20 to 29% in protective value
3: 30 to 39% in protective value
4: 40 to 49% in protective value
5: 50 to 59% in protective value
6: 60 to 69% in protective value
7: 70 to 79% in protective value
8: 80 to 89% in protective value
9: 90 to 99% in protective value
10: 100% in protective value The results of the above-described test demonstrate that the compounds of the present invention can produce the excellent controlling effect at the active-ingredient concentration of 50 ppm and at the chemical application rate of 50 mL; that among others, Compound Nos. 1-5, 1-7, 1-14, 1-15, 1-18, 1-21, 1-22, 1-28, 1-31, 1-34, 1-36, 1-37, 1-39, 1-44, 1-47, 2-6, 2-11, 2-36, 2-37, 3-3, 3-4, 3-5, 3-6, 3-11, 3-14, 3-15, 3-18, 3-21, 3-22, 3-23, 3-24, 3-25, 3-26, 3-27, 3-28, 3-33, 3-34, 3-36, 3-37, 3-39, 3-40, 3-43, 3-44, 3-47, 3-51, 3-52, 3-61, 3-63, 3-64, 3-65, 3-69, 3-70, 3-71, 3-74, 3-75, 3-76 and 3-77 showed the enhanced effect as high as 10 assessed according to the criteria of judgment, whereas the Control Compounds A and B, showing no effect as negligible as 0 assessed according to the criteria of judgment, failed to develop any controlling effect; and that out of the compounds of the present invention, Compound Nos. 1-21, 1-47, 3-3, 3-4, 3-6, 3-11, 3-14, 3-18, 3-21, 3-22, 3-23, 3-24, 3-25, 3-26, 3-27, 3-28, 3-33, 3-34, 3-36, 3-37, 3-39, 3-44, 3-47, 3-61, 3-63, 3-64, 3-65, 3-69, 3-70, 3-71, 3-74, 3-75, 3-76 and 3-77 at the active-ingredient concentration of 10 ppm and at the chemical application rate of 50 mL, exhibited the enhanced effect as high as 10 assessed according to the criteria of judgment.

Test Example 2

Test on the Controlling Effect Against Gray Mold of Cucumber Plant

A one-leaf aged cucumber plant (cultivar: Suyou) raised as a seedling in a pot of 9 cm in diameter was subject to foliar application with a diluted emulsion of the emulsifiable concentrate of the compound of the present invention prepared in accordance with Agrochemical Formulation Example 1, which diluted emulsion was produced by diluting the concentrate with water to the specifically determined volume. On the following day after the application, the cotyledon of the cucumber plant was inoculated by a paper disc of 6 mm in diameter impregnated with a suspension of spores of the causal fungus of gray mold of cucumber plant (*Botrytics cinerea*) as obtained by culture on the PSA medium, and maintained at 20° C. under humid conditions. Seven days after the inoculation, the fungus protective value (%) was determined in accordance with the equation (2), and the controlling effect was assessed according the criteria of judgment as set forth in Test Example 1.
Equation (2):

$$\text{Protective value (\%)} = X/Y \times 100 \quad (2)$$

where:
X; [(Diameter of the afflicted spot in non-treated section)− (Diameter of the afflicted spot in treated section)]
Y; (Diameter of the afflicted spot in non-treated section)

The results of the above-described test demonstrate that the compounds of the present invention produced the excellent controlling effect at the active-ingredient concentration of 200 ppm and at the chemical application rate of 50 mL; and that Compound Nos. 1-3, 1-5, 1-6, 1-8, 1-11, 1-14, 1-15, 1-17, 1-18, 1-21, 1-22, 1-28, 1-31, 1-33, 1-36, 1-38, 1-39, 1-40, 1-47, 2-6, 2-21, 3-3, 3-4, 3-5, 3-6, 3-7, 3-8, 3-11, 3-14, 3-15, 3-18, 3-21, 3-22, 3-23, 3-24, 3-25, 3-26, 3-27, 3-28, 3-31, 3-33, 3-34, 3-36, 3-37, 3-39, 3-40, 3-41, 3-42, 3-43, 3-51, 3-52, 3-61, 3-63, 3-64, 3-65, 3-69, 3-70, 3-71, 3-74, 3-75, 3-76, 3-77 and 4-6, among others, showed enhanced effect as high as 10 assessed according to the criteria of judgment, whereas the Control Compounds A and B, showing no effect as negligible as 0 assessed according to the criteria of judgment, failed to develop any controlling effect.

Test Example 3

Test on the Controlling Effect Against Powdery Mildew of Barley Plant

A one-leaf aged barley plant (the cultivar: Kantoh No. 6) raised as a seedling in a pot of 6 cm in diameter was subjected to foliar application with a diluted emulsion of the emulsifiable concentrate of the compound of the present invention prepared in accordance with Agrochemical Formulation Example 1, which diluted emulsion was produced by diluting the concentrate with water to the specifically determined volume. On the following day after the application, the barley plant was inoculated by sprinkling with spores as obtained from barley plants afflicted with the causal fungus of powdery mildew (*Blumeria graminis* f. sp. *hordei*), and maintained at 20° C. under humid conditions. Seven days after the inoculation, the controlling effect was assessed according the criteria of judgment as set forth in Test Example 1.

The results of the above-described test reveal that the Compounds of the present invention produced the excellent controlling effect at the active-ingredient concentration of 200 ppm and at the chemical application rate of 50 mL; that Compound Nos. 1-4, 1-5, 1-6, 1-11, 1-14, 1-21, 1-22, 1-31, 1-33, 1-36, 1-37, 1-38, 1-39, 1-47, 2-12, 2-14, 2-21, 2-22, 2-36, 2-38, 3-3, 3-4, 3-5, 3-6, 3-7, 3-8, 3-10, 3-11, 3-14, 3-15, 3-18, 3-21, 3-22, 3-23, 3-24, 3-25, 3-26, 3-27, 3-28, 3-29, 3-31, 3-33, 3-34, 3-36, 3-37, 3-38, 3-39, 3-40, 3-41, 3-42, 3-43, 3-47, 3-51, 3-52, 3-61, 3-63, 3-64, 3-65, 3-69, 3-70, 3-71, 3-74, 3-75, 3-76, 3-77, 4-6, 4-21 and 4-22, among others, showed the enhanced effect as high as 10 assessed according to the criteria of judgment, whereas the Control Compounds A and B, showing no activity as negligible as 0 assessed according to the criteria of judgment, failed to produce any controlling effect and the Control Compound C elicited the declined effect as low as 4 assessed according to the criteria of judgment; and that out of the compounds of the present invention, when applied at the active-ingredient concentration of 50 ppm and at the chemical application rate of 50 mL, Compound Nos. 1-23, 3-3, 3-4, 3-5, 3-6, 3-7, 3-8, 3-10, 3-11, 3-14, 3-18, 3-21, 3-22, 3-23, 3-24, 3-25, 3-26, 3-27, 3-28, 3-29, 3-31, 3-33, 3-34, 3-36, 3-37, 3-38, 3-39, 3-40, 3-41, 3-42, 3-43, 3-47, 3-61, 3-63, 3-64, 3-65, 3-69, 3-70, 3-71, 3-74, 3-75, 3-76, 3-77, 4-6, 4-21 and 4-22, among others, showed the enhanced effect as high as 10 assessed according to the criteria of judgment, whereas the Control Compound C, showing no effect as negligible as 0 assessed according to the criteria of judgment, failed to produce any controlling effect.

Test Example 4

Test on the Controlling Effect Against Brown Leaf Rust of Wheat Plant

A one-leaf aged wheat plant (the cultivar: Hokushin) raised as a seedling in a pot of 6 cm in diameter was subjected to foliar application with a diluted emulsion of the emulsifiable concentrate of the compound of the present invention prepared in accordance with Agrochemical Formulation Example 1, which diluted emulsion was produced by diluting the concentrate with water to the specifically determined volume. On the following day after the application, the wheat plant was inoculated by spraying of a suspension of spores as obtained from wheat plants afflicted with the causal fungus of brown leaf rust (*Puccinia recondita*), and maintained at 20° C. under humid conditions. Seven days after the inoculation, the controlling effect was assessed according the criteria of judgment as set forth in Test Example 1.

The results of the above-described test demonstrate that the compounds of the present invention produced the excellent controlling effect at the active-ingredient concentration of 200 ppm and at the chemical application rate of 50 mL; and that Compound Nos. 1-4, 1-5, 1-14, 1-15, 1-37, 1-38, 1-39, 1-44, 2-14, 2-21, 2-22, 2-36, 2-38, 3-3, 3-4, 3-5, 3-6, 3-7, 3-8, 3-10, 3-11, 3-14, 3-15, 3-18, 3-21, 3-22, 3-23, 3-24, 3-25, 3-26, 3-27, 3-28, 3-29, 3-31, 3-33, 3-34, 3-35, 3-36, 3-37, 3-38, 3-39, 3-40, 3-41, 3-42, 3-43, 3-44, 3-47, 3-51, 3-52, 3-61, 3-63, 3-64, 3-65, 3-69, 3-70, 3-71, 3-74, 3-75, 3-76, 3-77, 4-6, 4-21 and 4-22, among others, showed the enhanced effect as high as 10 assessed according to the criteria of judgment, whereas the Control Compound B, showing no effect as negligible as 0 assessed according to the criteria of judgment, failed to develop any controlling effect and the Control Compounds A and C both, exhibiting the reduced effect as low as 6 assessed according to the criteria of judgment, and produced the deteriorated controlling effect; and that out of the compounds of the present invention, when applied at the active-ingredient concentration of 50 ppm and at the chemical application rate of 50 mL, Compound Nos. 1-23, 3-3, 3-4, 3-6, 3-11, 3-18, 3-21, 3-22, 3-23, 3-24, 3-25, 3-26, 3-27, 3-28, 3-29, 3-31, 3-33, 3-34, 3-35, 3-37, 3-38, 3-40, 3-41, 3-42, 3-43, 3-47, 3-61, 3-63, 3-64, 3-65, 3-69, 3-70, 3-71, 3-74, 3-75, 3-76, 3-77, 4-6, 4-21 and 4-22, among others, showed the enhanced effect as high as 10 assessed according to the criteria of judgment, whereas the Control Compounds A and C, showing no effect as negligible as 0 assessed according to the criteria of judgment, failed to show any controlling effect.

INDUSTRIAL APPLICABILITY

The compounds of the present invention cause reduced loads of deleterious, harmful effects to the earth environment, while they exhibit a widened controlling spectrum against the diseases of plants for agricultural and horticultural uses at lowered chemical application rates, and consequently find useful application as a plant disease controlling agent with the excellent controlling effect.

The invention claimed is:

1. A pyrazinecarboxamide derivative, or its salts, represented by formula (I):

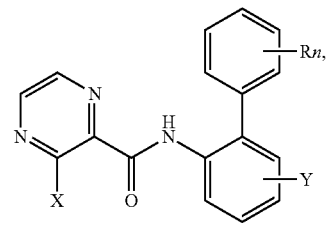

wherein:
X is
(i) a halogen atom, or
(ii) a ($C_1$-$C_3$)alkyl group which may be substituted with a halogen atom(s);
Y is
(i) a hydrogen or halogen atom, or
(ii) a ($C_1$-$C_3$)alkyl or ($C_1$-$C_3$)alkoxy group;
R is
(i) a hydrogen or halogen atom,
(ii) a cyano group,
(iii) a ($C_1$-$C_6$)alkyl group which may be substituted with a halogen atom(s),
(iv) a ($C_1$-$C_6$)alkoxy group which may be substituted with a halogen atom(s),
(v) a ($C_2$-$C_6$)alkenyloxy group which may be substituted with a halogen atom(s),
(vi) a ($C_2$-$C_6$)alkynyloxy group which may be substituted with a halogen atom(s),
(vii) a ($C_1$-$C_6$)alkylthio group which may be substituted with a halogen atom(s),
(viii) a ($C_1$-$C_6$)alkylsulfinyl group which may be substituted with a halogen atom(s),
(ix) a ($C_1$-$C_6$)alkylsulfonyl group which may be substituted with a halogen atom(s),
(x) a ($C_1$-$C_6$)alkoxycarbonyl group,
(xi) a phenyl group which may be substituted with a substituent(s) Z,
(xii) a phenoxy group which may be substituted with a substituent(s) Z,
(xiii) a pyridyloxy group which may be substituted with a substituent(s) Z, or
(xiv) a pyrimidyloxy group which may be substituted with a substituent(s) Z;
n is an integer of 1 to 5;
wherein, when n is an integer of 2 to 5, R may be the same or different and two adjacent Rs in formula (I) can be taken together to represent
(i) a ($C_3$-$C_5$)alkylene group which may be substituted with a substituent(s) Z,
(ii) a ($C_2$-$C_4$)alkyleneoxy group which may be substituted with a substituent(s) Z,
(iii) a ($C_2$-$C_4$)alkenyleneoxy group which may be substituted with a substituent(s) Z, or
(iv) a ($C_1$-$C_3$)alkylenedioxy group which may be substituted with a substituent(s) Z; and
Z is
(i) a hydrogen or halogen atom,
(ii) a cyano group,
(iii) a ($C_1$-$C_6$)alkyl group which may be substituted with a halogen atom(s), (iv) a $(C_2-C_6)$alkenyl group which may be substituted with a halogen atom(s), (v) a $(C_2-C_6)$alkynyl group which may be substituted with a halogen atom(s), (vi) a $(C_1-C_6)$alkoxy group which may be substituted with a halogen atom(s), (vii) a $(C_2-C_6)$alkenyloxy group which may be substituted with a halogen atom(s), (viii) a $(C_2-C_6)$alkynyloxy group which may be substituted with a halogen atom(s), (ix) a $(C_1-C_6)$alkylthio group which may be substituted with a halogen atom(s), (x) a $(C_1-C_6)$alkylsulfinyl group which may be substituted with a halogen atom(s), (xi) a $(C_1-C_6)$alkylsulfonyl group which may be substituted with a halogen atom(s), or (xii) a $(C_1-C_6)$alkoxycarbonyl, $(C_1-C_6)$alkoxyimino $(C_1-C_3)$alkyl or carbamoyl group, and when a plural number of Zs are present, the Zs may be the same or different.

2. The pyrazinecarboxamide derivative or its salts according to claim 1, wherein X is a chlorine, bromine or iodine atom, or a methyl, fluoromethyl, difluoromethyl or trifluoromethyl group.

3. The pyrazinecarboxamide derivative or its salts according to claim 1, wherein R is (i) a hydrogen or halogen atom, (ii) a cyano group, (iii) a $(C_1-C_6)$alkyl group which may be substituted with a halogen atom(s), (iv) a $(C_1-C_6)$alkoxy group which may be substituted with a halogen atom(s), (v) a $(C_2-C_6)$alkenyloxy group which may be substituted with a halogen atom(s), (vi) a $(C_2-C_6)$alkynyloxy group which may be substituted with a halogen atom(s), (vii) a $(C_1-C_6)$alkylthio group which may be substituted with a halogen atom(s), (viii) a $(C_1-C_6)$alkylsulfinyl group which may be substituted with a halogen atom(s), (ix) a $(C_1-C_6)$alkylsulfonyl group which may be substituted with a halogen atom(s), or (x) a $(C_1-C_6)$alkoxycarbonyl group; and when n is an integer of 2 to 5, R may be the same or different, and two adjacent Rs in formula (I) can be taken together to represent (i) a $(C_3-C_5)$alkylene or $(C_2-C_4)$alkyleneoxy group, or (ii) a $(C_1-C_3)$alkylenedioxy group which may be substituted with a halogen atom(s).

4. The pyrazinecarboxamide derivative or its salts according to claim 1, wherein Y is a hydrogen atom.

5. A plant disease controlling agent for agricultural and horticultural uses, comprising, as an active ingredient, the pyrazinecarboxamide derivative or its salts according to claim 1.

6. A method for controlling a plant disease, comprising treating a targeted plant or soil with an effective amount of the pyrazinecarboxamide derivative or its salts according to claim 1.

7. The pyrazinecarboxamide derivative or its salts according to claim 2, wherein R is (i) a hydrogen or halogen atom, (ii) a cyano group, (iii) a $(C_1-C_6)$alkyl group which may be substituted with a halogen atom(s), (iv) a $(C_1-C_6)$alkoxy group which may be substituted with a halogen atom(s), (v) a $(C_2-C_6)$alkenyloxy group which may be substituted with a halogen atom(s), (vi) a $(C_2-C_6)$alkynyloxy group which may be substituted with a halogen atom(s), (vii) a $(C_1-C_6)$alkylthio group which may be substituted with a halogen atom(s), (viii) a $(C_1-C_6)$alkylsulfinyl group which may be substituted with a halogen atom(s), or (ix) a $(C_1-C_6)$alkylsulfonyl group which may be substituted with a halogen atom(s), and when n is an integer of 2 to 5, R may be the same or different, and two adjacent Rs in formula (I) can be taken together to represent (i) a $(C_3-C_5)$alkylene or $(C_2-C_4)$alkyleneoxy group, or (ii) a $(C_1-C_3)$alkylenedioxy group which may be substituted with a halogen atom(s).

8. The pyrazinecarboxamide derivative or its salts according to claim 2, wherein Y is a hydrogen atom.

9. The pyrazinecarboxamide derivative or its salts according to claim 3, wherein Y is a hydrogen atom.

10. A plant disease controlling agent for agricultural and horticultural uses, comprising, as an active ingredient, the pyrazinecarboxamide derivative or its salts according to claim 2.

11. A plant disease controlling agent for agricultural and horticultural uses, comprising, as an active ingredient, the pyrazinecarboxamide derivative or its salts according to claim 3.

12. A plant disease controlling agent for agricultural and horticultural uses, comprising, as an active ingredient, the pyrazinecarboxamide derivative or its salts according to claim 4.

13. A method for controlling a plant disease, comprising treating a targeted plant or soil with an effective amount of the pyrazinecarboxamide derivative or its salts according to claim 2.

14. A method for controlling a plant disease, comprising treating a targeted plant or soil with an effective amount of the pyrazinecarboxamide derivative or its salts according to claim 3.

15. A method for controlling a plant disease, comprising treating a targeted plant or soil with an effective amount of the pyrazinecarboxamide derivative or its salts according to claim 4.

16. The pyrazinecarboxamide derivative or its salts according to claim 1, wherein X is a trifluoromethyl group;

Y is a hydrogen atom;

R is (i) a halogen atom, (ii) a cyano group, (iii) a $(C_1-C_4)$alkyl group which may be substituted with a halogen atom(s), (iv) a $(C_1-C_4)$alkoxy group which may be substituted with a halogen atom(s), (v) a $(C_2-C_4)$alkenyloxy group which may be substituted with a halogen atom(s),
(vi) a $(C_2-C_4)$alkynyloxy group which may be substituted with a halogen atom(s),
(vii) a $(C_1-C_4)$alkylthio group which may be substituted with a halogen atom(s),
(viii) a $(C_1-C_4)$alkylsulfinyl group which may be substituted with a halogen atom(s), or
(ix) a $(C_1-C_4)$alkylsulfonyl group which may be substituted with a halogen atom(s), and when n is an integer of 2 to 5, R may be the same or different, and two adjacent Rs in formula (I) can be taken together to represent a $(C_1-C_3)$alkylenedioxy group which may be substituted with a halogen atom(s).

* * * * *